United States Patent [19]

Takasu et al.

[11] 4,399,208

[45] Aug. 16, 1983

[54] ELECTROPHOTOGRAPHIC PHOTOSENSITIVE MEMBER

[75] Inventors: Yoshio Takasu, Tama; Norie Takebayashi, Tokyo; Kiyoshi Sakai, Mitaka; Minoru Mabuchi, Tokyo; Shozo Ishikawa, Sayama, all of Japan

[73] Assignee: Canon Kabushiki Kaisha, Tokyo, Japan

[21] Appl. No.: 319,269

[22] Filed: Nov. 9, 1981

[30] Foreign Application Priority Data

| Nov. 22, 1980 [JP] | Japan | 55-165065 |
| Nov. 22, 1980 [JP] | Japan | 55-165067 |
| May 7, 1981 [JP] | Japan | 56-68695 |
| May 9, 1981 [JP] | Japan | 56-69765 |

[51] Int. Cl.³ .............................................. G03G 5/04
[52] U.S. Cl. ...................................... 430/59; 430/73; 430/74; 430/76; 430/79
[58] Field of Search ...................... 430/58, 59, 73, 74, 430/76, 79

[56] References Cited

U.S. PATENT DOCUMENTS

| 4,150,987 | 4/1979 | Anderson et al. | 430/58 |
| 4,278,747 | 7/1981 | Murayama et al. | 430/59 |
| 4,284,698 | 8/1981 | Kazami et al. | 430/59 |
| 4,338,388 | 7/1982 | Sakai et al. | 430/59 |

Primary Examiner—Richard L. Schilling
Attorney, Agent, or Firm—Fitzpatrick, Cella, Harper & Scinto

[57] ABSTRACT

An electrophotographic photosensitive member is characterized by having a layer containing at least one hydrazone compound represented by the following formula [I] or [II]:

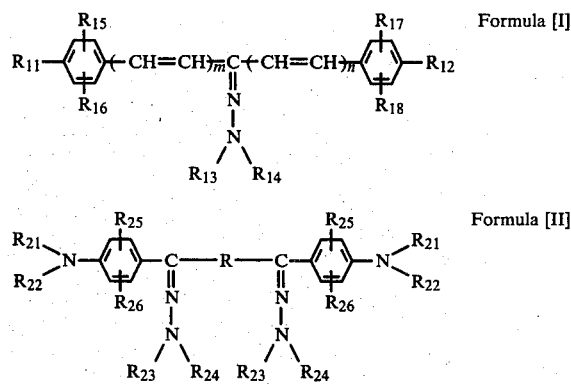

wherein $R_{11}$ and $R_{12}$ represent hydrogen, halogen, substituted or unsubstituted alkyl, alkoxy, substituted or unsubstituted aryloxy, or substituted amino, provided that at least one of $R_{11}$ and $R_{12}$ is substituted amino or alkoxy; $R_{13}$ and $R_{14}$ represent substituted or unsubstituted alkyl or substituted or unsubstituted aryl, provided that at least one of $R_{13}$ and $R_{14}$ is substituted or unsubstituted aryl, or $R_{13}$ and $R_{14}$, together with the nitrogen atom which links them, represent a nitrogen-containing heterocyclic ring; $R_{15}$, $R_{16}$, $R_{17}$, and $R_{18}$ represent hydrogen, halogen, substituted or unsubstituted alkyl, alkoxy, substituted or unsubstituted aryloxy, or substituted amino; m and n represent 0 or 1; $R_{21}$ and $R_{22}$ represent substituted or unsubstituted alkyl, or substituted or unsubstituted aryl, or $R_{21}$ and $R_{22}$, together with the nitrogen atom which links them, represent a five- or six-membered ring; $R_{23}$ and $R_{24}$ represent substituted or unsubstituted alkyl, substituted or unsubstituted aryl, or $R_{23}$ and $R_{24}$, together with the nitrogen atom which links them, represent a five- or six-membered ring; $R_{25}$ and $R_{26}$ represent hydrogen, halogen, nitro, substituted or unsubstituted alkyl, alkoxy, substituted or unsubstituted aryloxy, substituted or unsubstituted acyl, or substituted or unsubstituted amino; and R represents divalent organic residue.

51 Claims, 1 Drawing Figure

ELECTROPHOTOGRAPHIC PHOTOSENSITIVE MEMBER

BACKGROUND OF THE INVENTION

1. Field of the Invention

This invention relates to an electrophotographic photosensitive member provided with a photosensitive layer containing specific hydrazone compounds, and more particularly, it relates to an electrophotographic photosensitive member having enhanced sensitivity and improved durability to repeated operations.

2. Description of the Prior Art

Selenium, cadmium sulfide, zinc oxide, etc. have hitherto been known as photoconductive materials used for electrophotographic photosensitive members. In contrast their many advantages, for instance, chargeability to suitable potentials in a dark place, slight dissipation of charge in a dark place, and fast dissipation of charge being possible by light irradiation, these photosensitive materials are lack of film forming property in themselves, with a few exceptions such as the case of amorphous selenium, and have the disadvantage of poor retention of the charge given to their surface.

On the other hand, besides these inorganic photoconductive materials there are known organic ones including, for example, high-molecular photoconductive materials such as poly(N-vinylcarbazole), N-acrylamidemethylcarbazole polymer disclosed in Japan Pat. Appl. Laid-open No. 85337 (1975), and 6-vinylindole(2,3-6)quinoxaline polymer disclosed in Japan Pat. Appl. Laid-open No. 93432 (1975); and low-molecular photoconductive materials such as 2-aza-9-fluoroenones (Japan Pat. Appl. Laid-Open No. 71236/1973), triarylpyrazolines (U.S. Pat. No. 3,824,099), bis(p-dialkylaminostyryl)phenyl (Japan Pat. Appl. Laid-open No. 31773/1975), 2, 6-bisstyrylpryidines (Japan Pat. Appl. Laid-open No. 94828/1976), spiro-pyrazolines (Japan Pat. Appl. Laid-open No. 112637/1979), N-(p-dialkylaminophenyl)carbazoles (Japan Pat. App. Laid-open No. 119925/1979), 2, 5-bis(p-dialkylaminophenyl)-1, 3, 4-oxadiazoles (Japan Pat. Appl. Laid-open No. 121742/1979), bis(p-dialkylaminophenyl)alkanes (Japan Pat. Appl. Laid-open No. 17105/1980), bis(p-dialkylaminophenyl)quinolylalkanes (Japan Pat. Appl. Laid-open No. 108667/1980), hydrazone compounds (U.S. Pat. No. 4,150,987), 9-styrylanthracene compounds (Japan Pat. Appl. Laid-open Nos. 94828/1976 and 94829/1976), and 4-chlorooxazole compounds (Japan Pat. Appl. Laid-open No. 53278/1980). However, these organic photoconductive materials are not of practical use because of their low sensitivity.

Such being the case, in recent years laminated members have offered which comprise two photosensitive layers provided with separate functions, that is, a charge generation layer and a charge transport layer which contains an organic photoconductive material. Electrophotographic photosensitive members comprising such photoconductive layers of laminate structure have been improved in certain points such as sensitivity to visible light, charge bearing capacity, and surface strength, in which photosensitive members employing organic photoconductive materials had been deficient. Such improved electrophotographic photosensitive members have been disclosed, for example, in U.S. Pat. No. 3,837,851 (Japan Pat. Appl. Laid-open No. 105537/1974), U.K. Pat. No. 1,453,024 (Japan Pat. Appl. Laid-open No. 90827/1976), and U.S. Pat. Nos. 3,484,237 and 3,871,882.

Electrophotographic photosensitive members employing existing organic photoconductive materials are however still unsatisfactory in sensitivity and disadvantageous in that notable variations of surface potential are caused by repeated charging and exposure, and in particular increase of potential in light area and decrease of potential in dark area are remarkable in that case.

SUMMARY OF THE INVENTION

An object of this invention is to provide organic photoconductive materials of high sensitivity comprising novel hydrazone compounds.

Another object of the invention is to provide electrophotographic photosensitive members of high sensitivity and enhanced durability.

Another object of the invention is to provide a charge transport layer having an improved charge-transporting function.

Another object of the invention is to provide photosensitive layer, highly sensitive as well as highly durable, of laminate structure constituted of a charge generation layer and a charge transport layer.

Another object of the invention is to provide electrophotographic photosensitive members wherein increase of light portion potential and decrease of dark portion potential in repeated operations are inhibited.

According to the present invention, there is provided an electrophotographic photosensitive members characterized by having a layer containing at least one hydrazone compound represented by the following formula [I] or [II]:

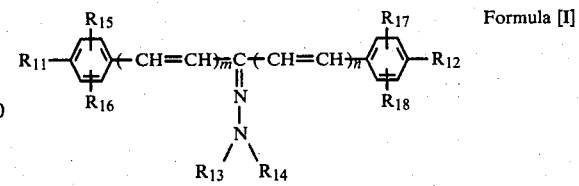

wherein $R_{11}$ and $R_{12}$ represent hydrogen, halogen, substituted or unsubstituted alkyl, alkoxy, substituted or unsubstituted aryloxy, or substituted amino, provided that at least one of $R_{11}$ and $R_{12}$ is substituted amino or alkoxy; $R_{13}$ and $R_{14}$ represent substituted or unsubstituted alkyl or substituted or unsubstituted aryl, provided that at least one of $R_{13}$ and $R_{14}$ is substituted or unsubstituted aryl, or $R_{13}$ and $R_{14}$, together with the nitrogen atom which links them, represent a nitrogen-containing heterocyclic ring; $R_{15}$, $R_{16}$, $R_{17}$, and $R_{18}$ represent hydrogen, halogen, substituted or unsubstituted alkyl, alkoxy, substituted or unsubstituted aryloxy, or substituted amino; m and n represent 0 or 1; $R_{21}$ and $R_{22}$, represent substituted or unsubstituted alkyl, or substituted or unsubstituted aryl, or $R_{21}$ and $R_{22}$, together with the nitrogen atom which links them, represent a five- or six-membered ring; $R_{23}$ and $R_{24}$ represent substituted or unsubstituted alkyl, substituted or unsubstituted aryl, or $R_{23}$ and $R_{24}$, together with the nitrogen atom which links them, represent a five- or six-membered ring; $R_{25}$ and $R_{26}$ represent hydrogen, halogen, nitro, substituted or unsubstituted alkyl, alkoxy, substituted or unsubstituted aryloxy, substituted or unsubstituted acyl, or substituted or unsubstituted amino; and R represents divalent organic residue.

BRIEF DESCRIPTION OF THE DRAWING

The FIGURE is a schematic illustration of the device used for forming charge generation layers in Examples 11, 21, 36, and 47.

DETAILED DESCRIPTION OF THE INVENTION

Figure 1:
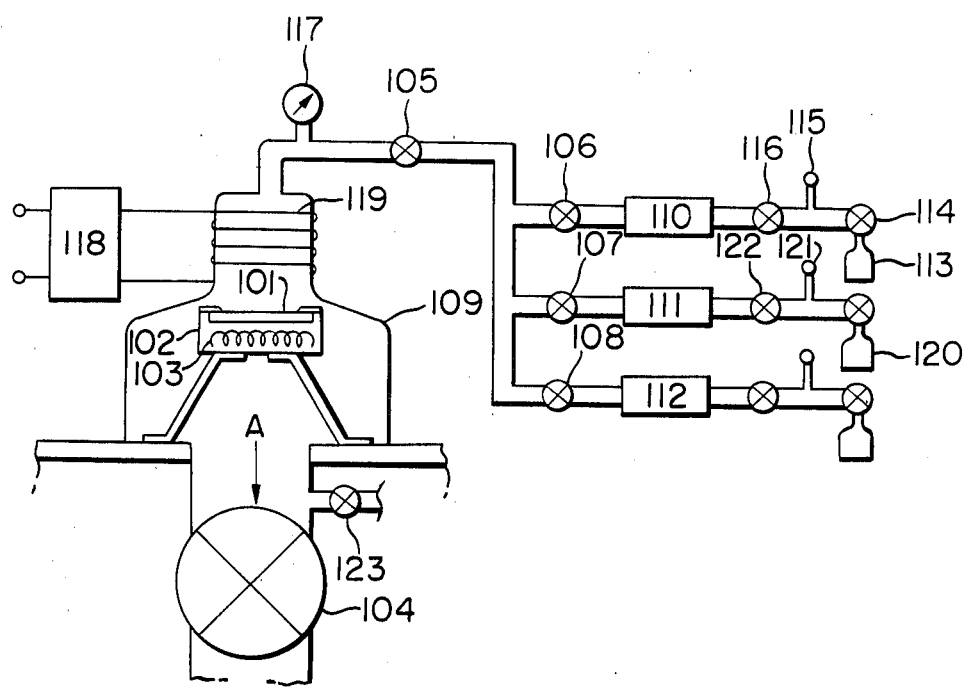

The specific hydrazone compounds used in this invention are represented by the following formula [I] or [II]:

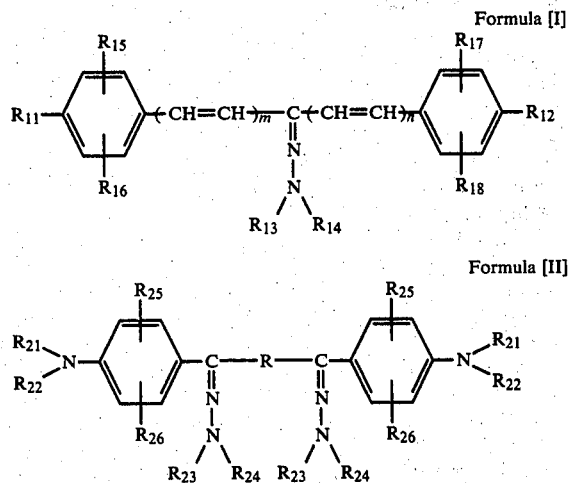

In these formulas, $R_{11}$ and $R_{12}$ represent hydrogen, halogen (e.g., chlorine, bromine, etc.), substituted or unsubstituted alkyl (e.g., methyl, ethyl, n-propyl, iso-propyl, n-butyl, sec-butyl, t-butyl, n-amyl, t-amyl, n-octyl, benzyl, methylbenzyl, chlorobenzyl, allyl, vinylmethyl, etc.), alkoxy (e.g., methoxy, ethoxy, butoxy, etc.), substituted or unsubstituted aryloxy (e.g., phenoxy, methylphenoxy, ethylphenoxy, dimethylphenoxy, chlorophenoxy, etc.), or substituted amino (e.g., N, N-dimethylamino, N, N-diethylamino, N, N-diprophylamino, N, N-dibutylamino, N, N-dibenzylamino, N-methyl-N-ethylamino, pyrrolidino, piperidino, morpholino, etc.), and at least one of $R_{11}$ and $R_{12}$ is substituted amino or alkoxy.

$R_{13}$ and $R_{14}$ represent substituted or unsubstituted alkyl (e.g., methyl, ethyl, n-propyl, n-butyl, t-butyl, n-octyl, t-octyl, benzyl, methylbenzyl, chlorobenzyl, allyl, etc.), or substituted or unsubstituted aryl (e.g., phenyl, tolyl, xylyl, chlorophenyl, methoxyphenyl, naphthyl, etc.), and at least one of $R_{13}$ and $R_{14}$ is substituted or unsubstituted aryl, and $R_{13}$ and $R_{14}$ may also, together with the nitrogen atom which links them, form a nitrogen-containing heterocyclic ring (e.g., carbazol ring, morpholine ring, piperidine ring, pyrrolidine ring etc.).

$R_{15}$, $R_{16}$, $R_{17}$, and $R_{18}$ represent hydrogen, halogen (e.g., fluorine, chlorine, or bromine), alkoxy (e.g., methoxy, ethoxy, butoxy etc.), substituted or unsubstituted alkyl (e.g., methyl, ethyl, n-propyl, n-butyl, t-butyl, n-octyl, t-octyl, benzyl, methylbenzyl, allyl, etc.), aryloxy (e.g., phenoxy, methylphenoxy, chlorophenoxy, acetylphenoxy, etc.), or substituted amino (e.g., N, N-dimethylamino, N, N-diethylamino, or N, N-dipropylamino); and m and n represent 0 or 1.

$R_{21}$, $R_{22}$, $R_{23}$ and $R_{24}$ represent substituted or unsubstituted alkyl (e.g., methyl, ethyl, n-propyl, iso-propyl, n-butyl, n-amyl, t-amyl, n-octyl, benzyl, chlorobenzyl, allyl, vinylmethyl, etc.) or substituted or unsubstituted aryl (e.g. phenyl, tolyl, xylyl, methoxyphenyl, chlorophenyl, etc.), and $R_{21}$ and $R_{22}$ together with the nitrogen which links $R_{21}$ and $R_{22}$, and $R_{23}$ and $R_{24}$ together with nitrogen which links $R_{23}$ and $R_{24}$ may also form five- or six-membered heterocyclic rings (e.g., morpholine ring, piperidine ring, pyrrolidine ring, carbazole ring etc.), respectively.

$R_{25}$ and $R_{26}$ represent hydrogen, halogen (e.g., fluorine, chlorine, or bromine), nitro, substituted or unsubstituted alkyl, (e.g., methyl, ethyl, n-propyl, iso-prophyl, n-amyl, t-amyl, n-octyl, benzyl, allyl, etc.), alkoxy, (e.g., methoxy, ethoxy, butoxy, etc.), substituted or unsubstituted aryloxy (e.g., phenoxy, methylphenoxy, ethylphenoxy, dimethylphenoxy, chlorophenyl, etc.), substituted or unsubstituted acyl (e.g., acetyl, propyonyl, benzoyl, methylbenzoyl, etc.), or substituted or unsubstituted amino (e.g., amino, N, N-dimethylamino, N, N-diethylamino, N-methyl-N-ethylamino, N, N-dipropyl-amino, acetylamino, etc.).

R represents divalent organic residue, preferably substituted divalent hydrocarbon residue, saturated or unsaturated, wherein the preferred substitutents include halogen (e.g., fluorine, chlorine, and bromine), hydroxyl hydroxy, carboxyl, phenyl, carboxyphenyl, and the like.

Examples of said divalent organic residue are as follows:

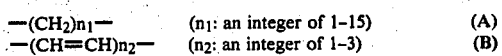

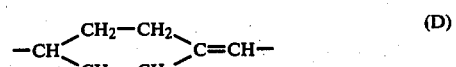

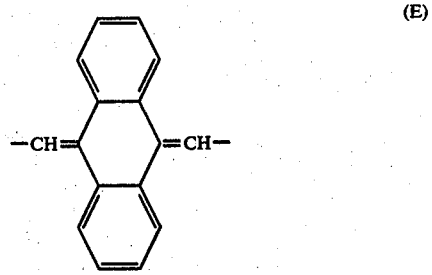

R may be also substituted or unsubstituted arylene (e.g., phenylene, naphthylene, or anthrylene), wherein the preferred substituents include halogen (e.g., fluorine, chlorine, and bromine), alkyl (e.g., methyl, ethyl, propyl, and butyl), and the like.

Examples of said arylene are as follows:

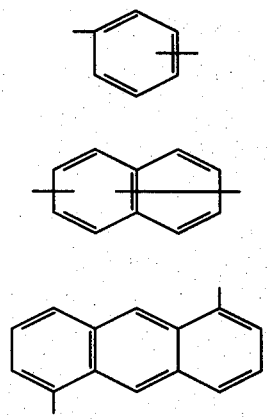

(G)

(H)

(J)

More specifically, there may be cited p-phenylene, m-phenylene, o-phenylene, 1,3-naphthylene, 1,5-naphthylene, 1,4-naphthylene, 1,6-naphthylene, 2,7-naphthylene, and 2,6-naphthylene.

Among the compounds represented by formula [I], compounds of which m and n are both zero are represented by the following formula [I]:

General formula (1)

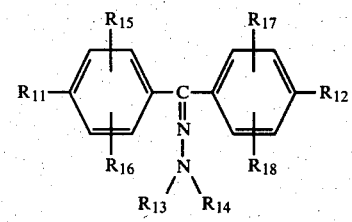

Similarly, compounds of which m is 1 are represented by the following formula (2):

General formula (2)

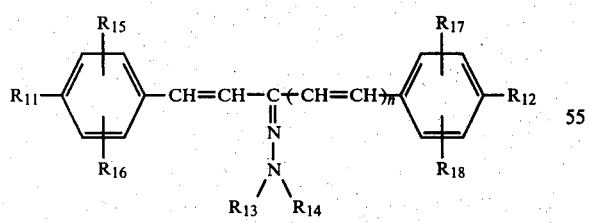

In these formulas, $R_{11}$, $R_{12}$, $R_{13}$, $R_{14}$, $R_{15}$, $R_{16}$, $R_{17}$, and $R_{18}$ are as defined above.

Typical examples of the hydrazone compounds usable in the electrophotographic photosensitive members of this invention are shown below:

Examples of compounds represented by the above-mentioned general formula (1):

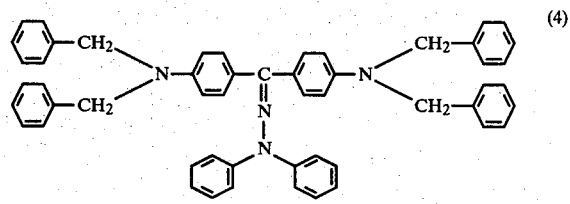

(1)

(2)

(3)

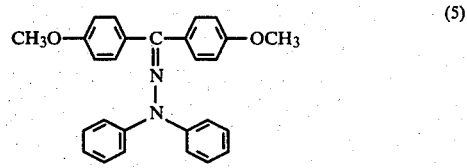

(4)

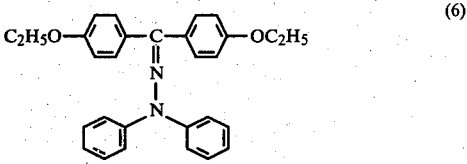

(5)

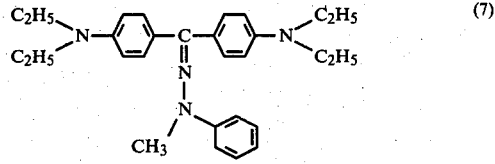

(6)

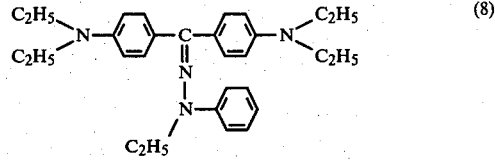

(7)

(8)

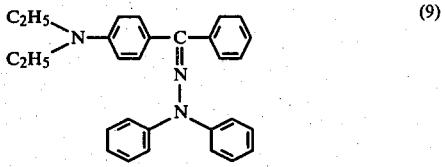

(9)

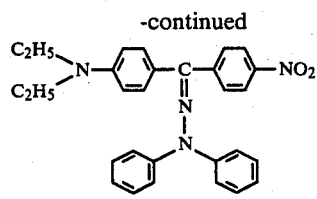 (10)
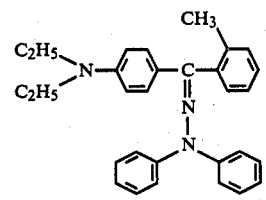 (11)
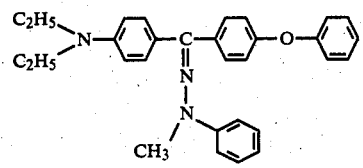 (12)
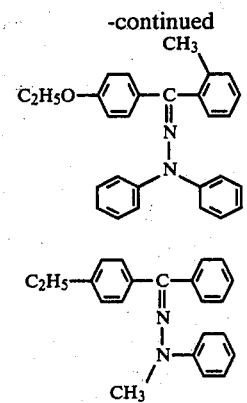 (13)
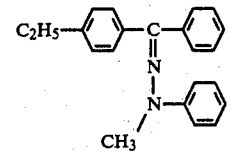 (14)
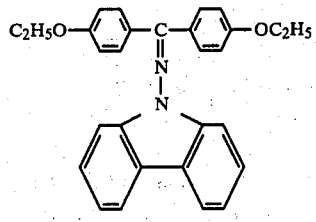 (15)
Examples of compounds represented by the general formula (2):
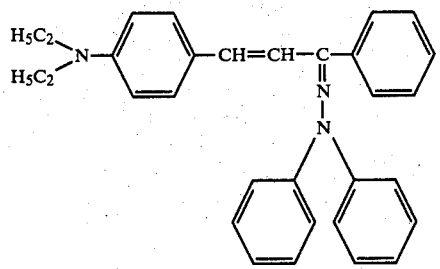 (16)
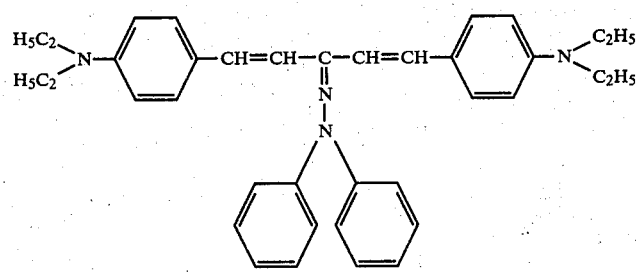 (17)
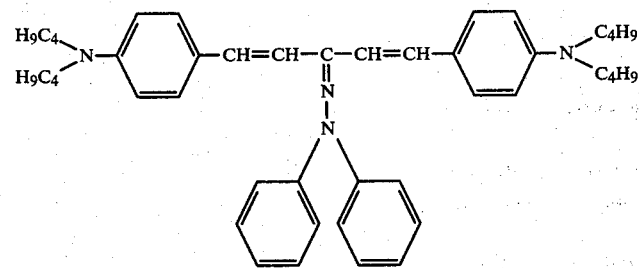 (18)

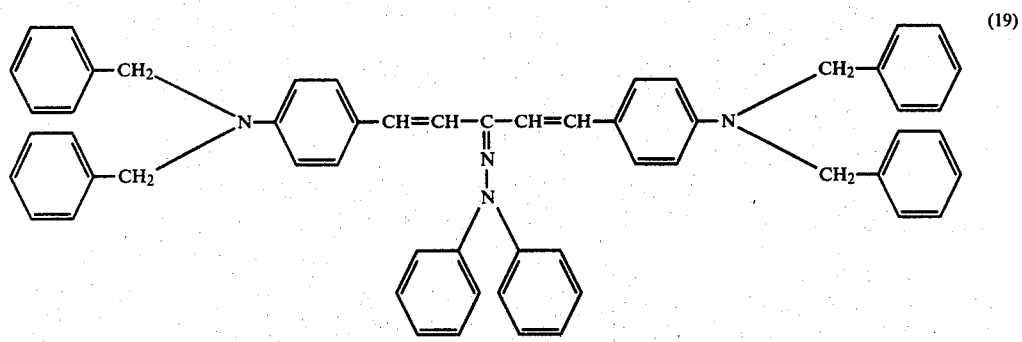
(19)
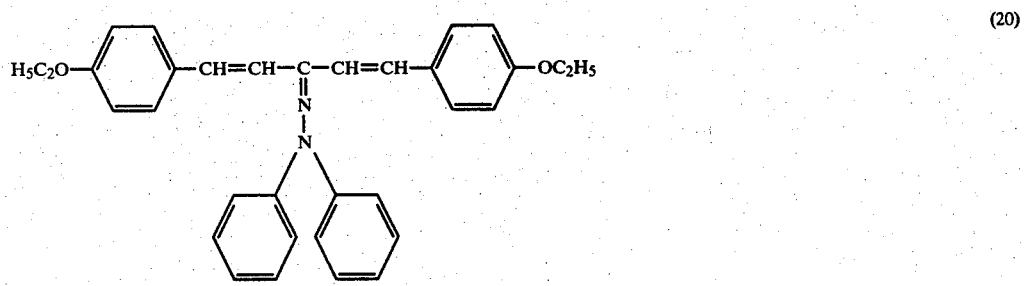
(20)
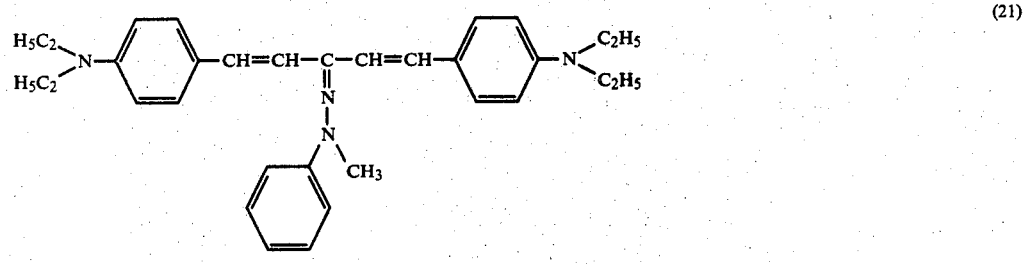
(21)
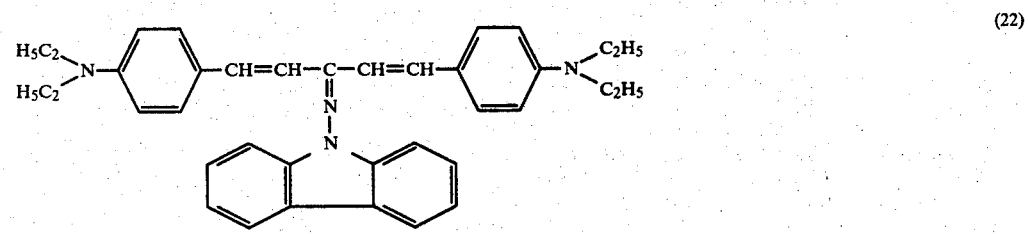
(22)
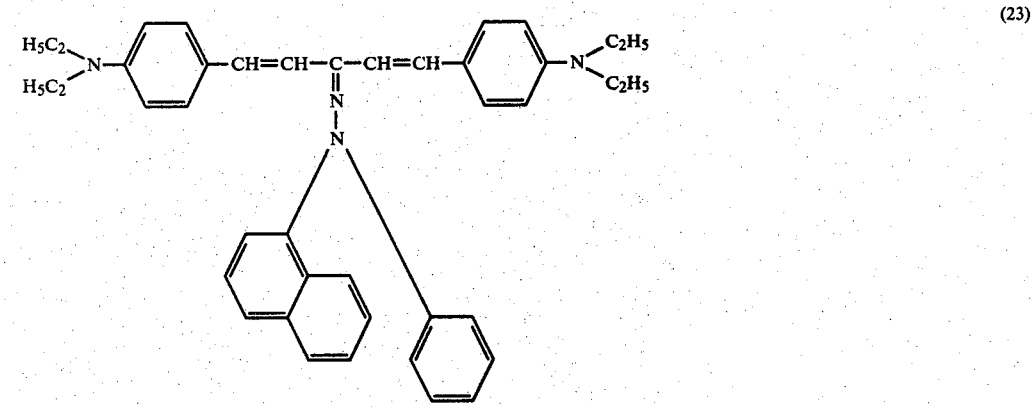
(23)

-continued
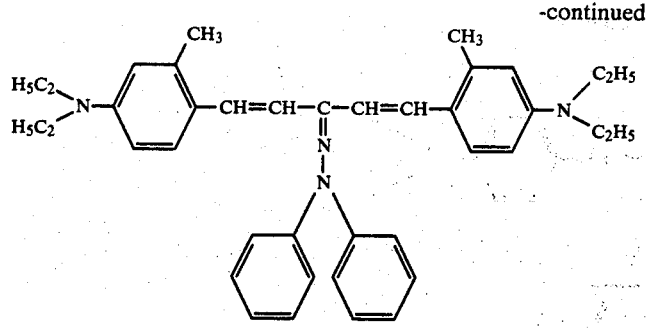
(24)
Examples of compounds represented by formula [II]:
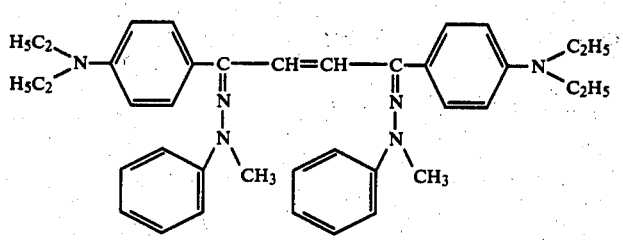
(25)
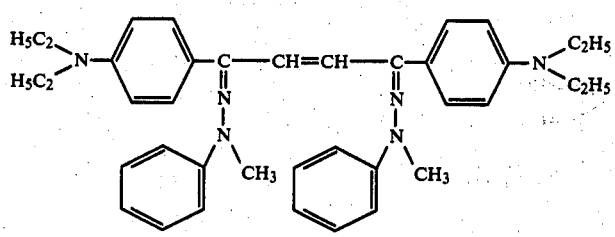
(26)
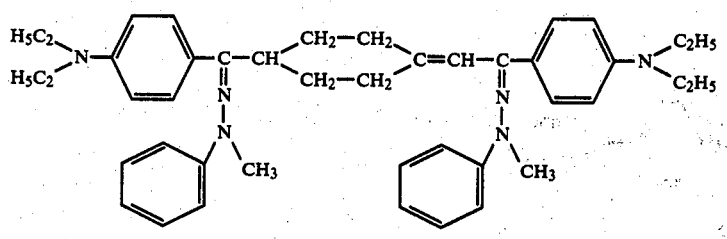
(27)
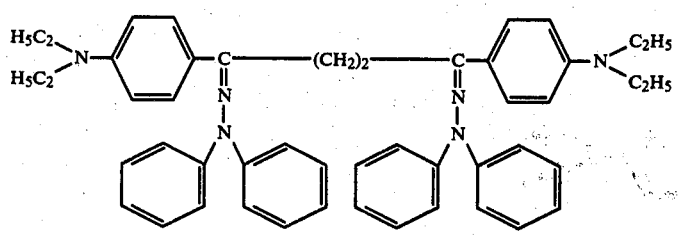
(28)
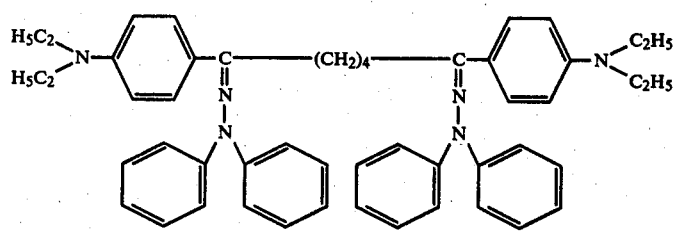
(29)

-continued
(30)
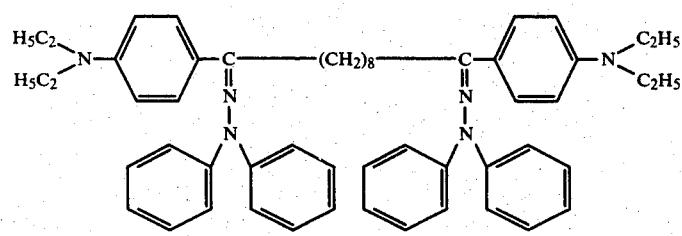
(31)
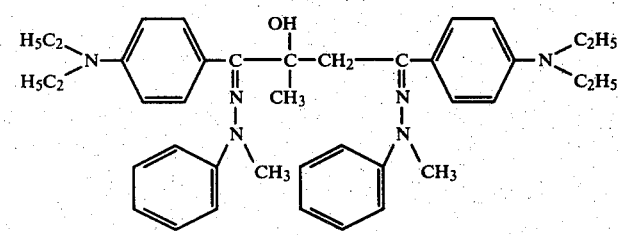
(32)
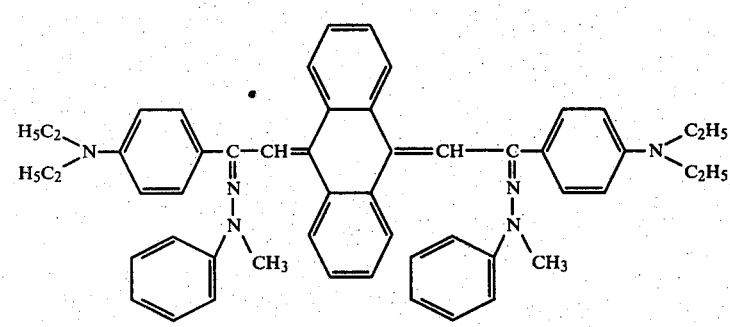
(33)
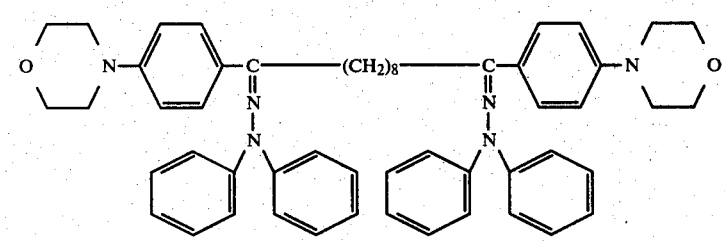
(34)
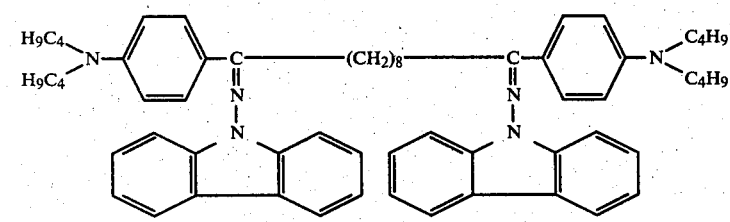
(35)
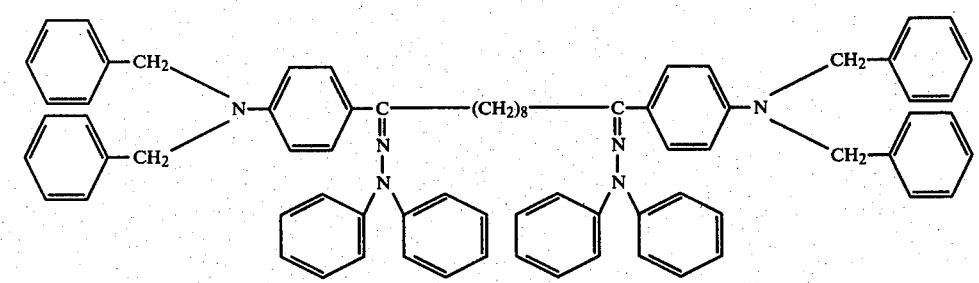

-continued
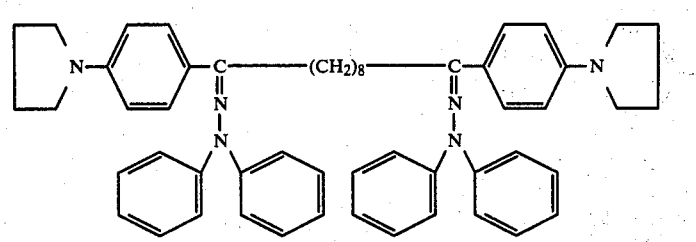
(36)
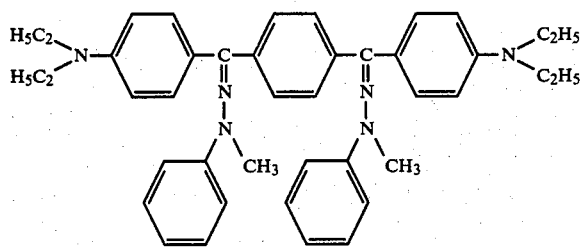
(37)
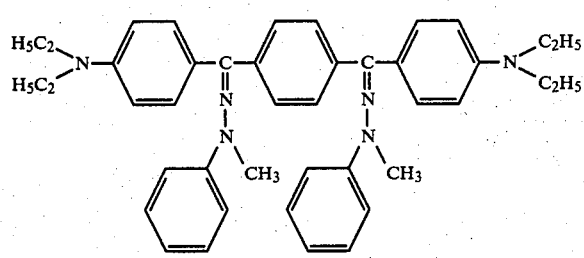
(38)
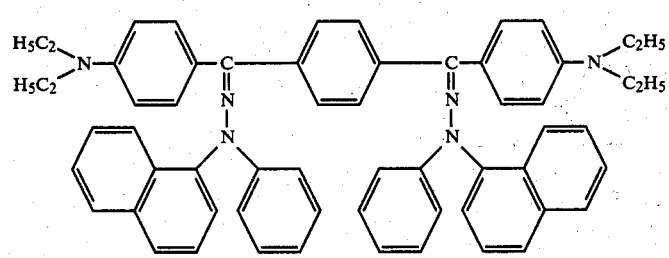
(39)
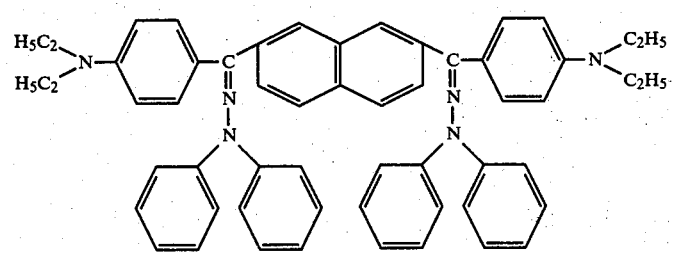
(40)
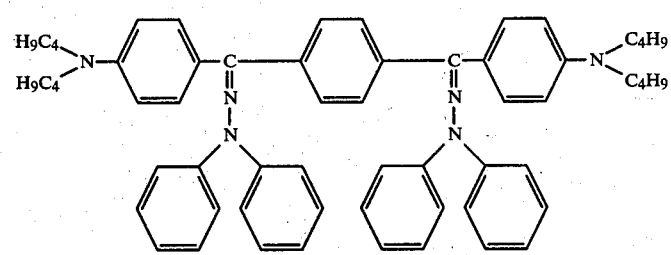
(41)

-continued
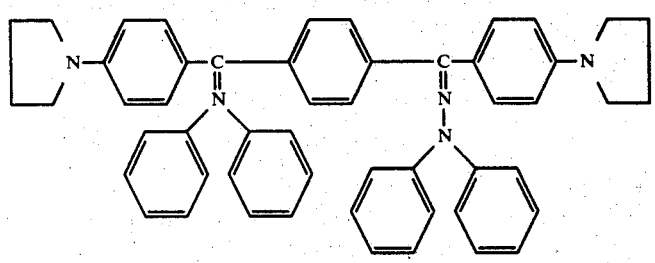
(42)
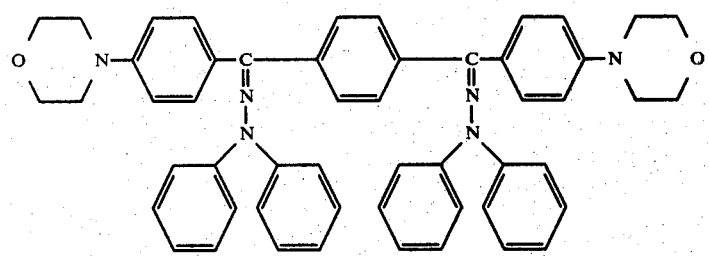
(43)
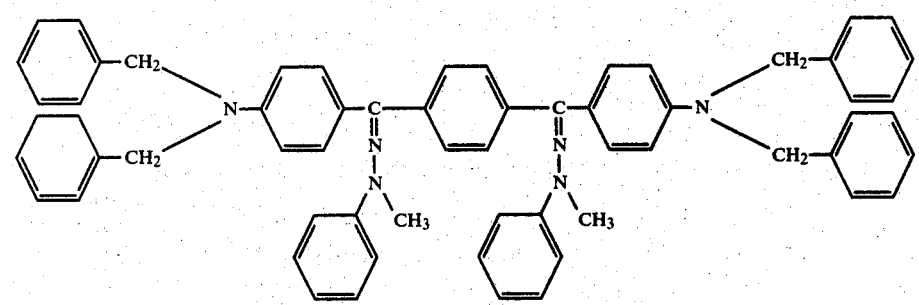
(44)
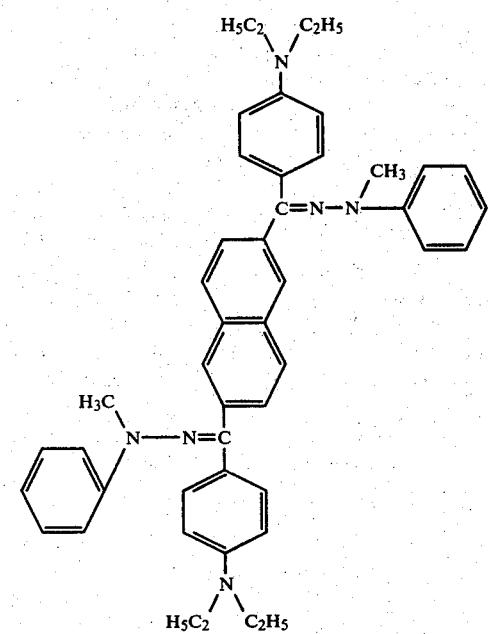
(45)
These compounds can be used alone or in combination with others.
They can be readily prepared by condensation of ketone compounds with hydrazine compounds.
For example, compounds represented by the general formula (1) above can be synthesized by condensation of a ketone represented by the formula

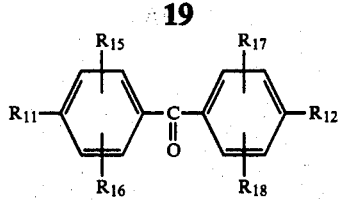

with a hydrazine compound represented by the formula

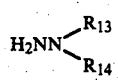

wherein $R_{11}$–$R_{18}$ are as defined above.

Compounds represented by the general formula (2) above in which n=0 can be synthesized by condensation of an acetophenone compound represented by the formula

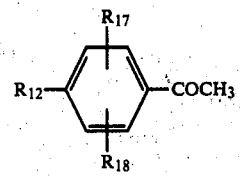

with a benzaldehyde compound represented by the formula

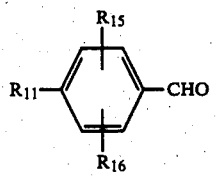

wherein $R_{11}$–$R_{18}$ are as defined above, and then by condensation of the ketone thus obtained, which is represented by the formula

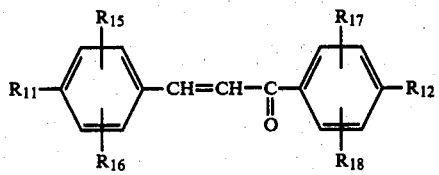

($R_{11}$, $R_{12}$, $R_{15}$–$R_{18}$: the same as the above) with a hydrazine compound represented by the above formula.

Compounds of the general formula (2) in which n=1 can be readily synthesized by condensation of a ketone of the formula

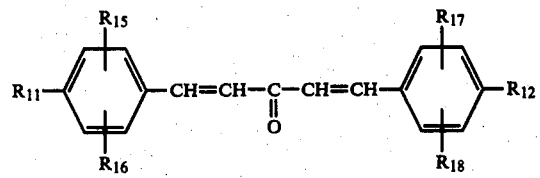

($R_{11}$, $R_{12}$, $R_{15}$–$R_{18}$: the same as the above) with a hydrazine compound of the above formula.

Compounds of formula [II] shown above can be synthesized by reaction of a dicarboxylic acid dichloride of the formula

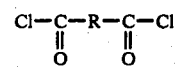

(R: the same as the above) with a N-substituted aminophenyl and then by condensation of the diketone thus obtained, which is represented by the formula

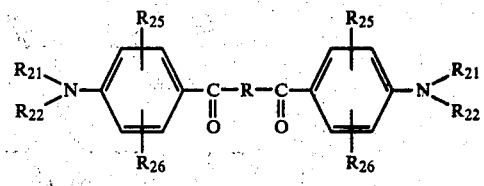

(R, $R_{21}$, $R_{22}$, $R_{25}$, $R_{26}$: the same as the above), with a hydrazine compound of the formula

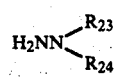

($R_{23}$, $R_{24}$: the same as the above).

The dicarboxylic acid dichlorides usable here include those of the following acids: fumaric acid, maleic acid, malonic acid, citraconic acid, itaconic acid, tetrahydrophthalic acid, hexahydrophthalic acid, succinic acid, adipic acid, azelaic acid, sebacic acid, malic acid, glutaric acid, ethoxysuccinic acid, citramalic acid, oxalic acid, anthracenemaleic anhydride adduct, β-naphtholmaleic anhydride adduct, phthalic acid, isophthalic acid, terephthalic acid, 1,3-dicarboxynaphthalene, 1,5-dicarboxynaphthalene, 1,4-dicarboxynaphthalene, 1,6-dicarboxynaphthalene, 2,6-dicarboxynaphthalene, 1,7-dicarboxynaphthalene, 1,5-dicarboxyanthracene, and the like.

The solvents usable in the above condensation reaction include various kinds of organic solvents, of which suitable ones are methanol, ethanol, 1,4-dioxane, tetrahydrofuran, methyl "Cellosolve", ethyl "Cellosolve", dimethylformamide, acetic acid, and the like.

Now, methods of synthesizing typical hydrazone compounds used in this invention are illustrated.

Synthesis Example 1 (Compound No. 2)

A solution of 27.7 g (0.14 mol) of N-nitrosodiphenyl amine

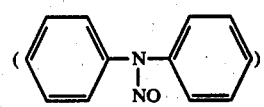

in 230 ml of acetic acid was cooled to 10° C. and reduced by adding 87.5 g (1.14 mol) of zinc powder in limited amounts. The resulting liquid was filtered and poured into water to isolate a hydrazine compound.

Then, the hydrazine compound was dissolved in 110 ml of ethanol, 45.4 g (0.14 mol) of the ketone compound of the formula

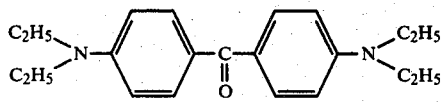

was added, and the mixture was stirred for 30 minutes. The reaction mixture was poured into water, and the yellow precipitate obtained was recrystallized from methyl ethyl ketone. Thus, 18.9 g of yellow crystals were obtained (yield on the nitroso compound: 27.5%).

| Elementary analysis: | | |
|---|---|---|
| | Calcd. for $C_{33}H_{38}N_4$ (%) | Found (%) |
| C | 80.82 | 80.55 |
| H | 7.76 | 7.79 |
| N | 11.42 | 11.66 |

Synthesis Example 2 (Compound No. 16)

Condensation reaction was effected between 48 g (0.4 mol) of acetophenone and 70.8 g (0.4 mol) of 4-N,N-diethylaminobenzaldehyde in dimethylformamide. The reaction mixture was poured into water and the resulting ketone compound was isolated.

Then, 41.9 g (0.15 mol) of this ketone compound was added to a solution of 27.6 g (0.15 mol) of the hydrazine compound prepared in Synthesis Example 1, in 120 ml of ethanol. After stirred for one hour, the reaction mixture was poured into water and the yellow precipitate obtained was recrystallized from methyl ethyl ketone. Thus, 12.3 g of yellow crystals were obtained (yield on the ketone compound: 21.4%).

| Elementary analysis: | | |
|---|---|---|
| | Calcd. for $C_{31}H_{31}N_3$ (%) | Found (%) |
| C | 83.60 | 83.52 |
| H | 7.00 | 7.07 |
| N | 9.40 | 9.41 |

Synthesis Example 3 (Compound No. 37)

A diketone compound was prepared by reacting 0.3 mol of 1,4-benzenedicarbonyl dichloride and 0.6 mol of N,N-diethylaniline.

On the other hand, a hydrazine compound was prepared by dissolving 19 g (0.14 mol) of N-nitroso-N-methylaniline

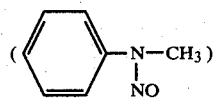

in 230 ml of acetic acid, reducing the nitroso compound by adding 87.5 g (1.14 mol) of zinc powder in limited amounts to the solution cooled to 10° C., filtering the resulting mixture, and pouring the filtrate into water to isolate the hydrazine compound produced.

Then, 30 g (0.07 mol) of the above diketone compound was added to a solution of the above hydrazine compound in 110 ml of ethanol. After one-hour stirring, the reaction mixture was poured into water, and the resulting yellow precipitate was recrystallized from methyl ethyl ketone. Thus, 13.6 g of yellow crystals were obtained (yield on the nitroso compound: 30.6%).

| Elementary analysis: | | |
|---|---|---|
| | Calcd. for $C_{42}H_{48}N_6$ (%) | Found (%) |
| C | 79.25 | 79.21 |
| H | 7.55 | 7.59 |
| N | 13.20 | 13.20 |

The electrophotographic photosensitive member containing the foregoing hydrazone compounds can be applied to any type of electrophotographic photosensitive member employing organic photoconductive materials. Among them, the following types are preferred.

(1) A charge-transfer complex is formed by combining an electron donating substance and an electron-accepting substance.
(2) An organic photoconductor is sensitized by adding a dye.
(3) A pigment is dispersed in a hole-matrix.
(4) Functions are allotted to a charge generation layer and a charge transport layer.
(5) A dye-resin co-crystalline complex and an organic photoconductor are used as primary components.
(6) An organic or inorganic charge-generating material is incorporated into a charge-transfer complex.

Particularly favarable types are (3) to (6). Additionally when applied to photosensitive members of type (4), that is, when used as a charge-transporting material in the charge transport layers of photosensitive members comprising two layers of separate functions, charge generation and charge transport, the hydrazone compounds of this invention improve the sensitivity and lower the residual potential. This is caused by the capability of said hydrazone compounds to effectively transport the charge generated in the charge generation layer when the layer containing said hydrazone compound is laid in contact with the charge generation layer. Furthermore, it is also possible in this case to suppress the reduction of sensitivity and the rise of residual potential in repeated operations to an actually negligible level. Accordingly, the photosensitive member of type (4) will be described in detail, but the hydrazone compounds of this invention can be also applied favorably to other types of photosensitive members.

The charge transport layer according to this invention is preferably formed by coating a solution of a charge-transporting material comprising foregoing hydrazone compounds and of a binder in a suitable solvent, and drying the coating. The binders used here include, for example, polyethylene, polypropylene, acrylic resins, methacrylic resins, vinyl chloride resin, vinyl acetate resin, phenolic resins, epoxy resins, polyester resins, alkyd resins, polycarbonates, polyurethanes, and copolymers comprising two or more kinds of repeating units of these resins. Among them, particularly preferred ones are polyester resins and polycarbonates. A photoconductive polymer such as poly(N-vinylcarbazole) having charge transporting function in itself also can be used as a binder for this purpose.

Compounding ratio of this binder to the charge-transporting compound is preferably 100:10–500 by weight. Thickness of the charge transport layer is 2–100μ, preferably 5–30μ.

The charge transport layer in this invention can contain various kinds of additives for example, diphenyl, chlorodiphenyl, o-terphenyl, p-terphenyl, dibutyl phthalate, dimethylglycol phthalate, dioctyl phthalate, triphenyl phosphate, methylnaphthalene, benzophenone, chlorinated paraffin, dilauryl thiodipropionate, 3,5-dinitrosalicylic acid, various fluorocarbons, and the like.

The solvents used in forming the charge transport layer in this invention include many organic solvents. Typical examples thereof are aromatic hydrocarbons such as benzene, naphthalene, toluene, xylene, mesitylene, chlorobenzene, and the like; ketones such as acetone, 2-butanone, and the like; halogenated aliphatic hydrocarbons such as methylene chloride, chloroform, ethylene chloride, and the like; cyclic or linear ethers such as tetrahydrofuran, ethyl ether, and the like; and mixtures of these solvents.

As the charge-generating material, any substance can be used provided that it generates charge carriers at a high efficiency on absorbing light. The preferred materials include inorganic substances such as selenium, selenium-tellurium, selenium-arsenic, cadmium sulfide, amorphous silicon, and the like, and organic substances such as pyrylium dyes, thiopyrylium dyes, triarylmethane dyes, thiazine dyes, cyanine dyes, phthalocyanine pigments, perylene pigments, indigo dyes, thioindigo dyes, quinacridone pigments, squaric acid pigments, azo pigments, polycyclic quinone pigments, and the like. Thickness of the charge generation layer is up to 5μ, preferably 0.05-3μ.

The charge generation layer can be formed by vacuum deposition, sputtering, glow discharge, or usual coating depending upon the kinds of charge-generating materials.

The coating may be performed by applying a binder-free charge-generating material, a dispersion of charge-generating material containing a binder resin, or a homogeneous solution of charge-generating material and binder.

In the above second and third cases, that is, when a binder is used for the coating of charge-generating material, the content of binder in the charge generation layer is desired up to 80%, preferably 40% or less, by weight because higher contents of binder affect the sensitivity adversely.

The binders applicable for the charge generation layer include poly(vinyl butyral), poly(methyl methacrylate), polyesters, poly(vinylidene chloride), chlorinated rubbers, polyvinyltoluene, styrene-maleic anhydride copolymer, polystyrene, poly(vinyl chloride), ethylcellulose, polyamides, and styrene-butadiene copolymer.

The following monoazo, disazo, and trisazo pigments can be cited as specific examples of the charge-generating materials: disazo pigments having a biphenyl skeleton disclosed in Japan Pat. Appl. Laid-open Nos. 70538 (1973), 4241 (1977), 119926 (1979), and 119927 (1979); disazo pigments having a stilben skeleton disclosed in Japan Pat. Appl. Laid-open Nos. 8832 (1977) and 20737 (1979); disazo pigments having a styrylstilben skeleton disclosed in U.S. Pat. Nos. 4256821 and 4272598; disazo pigments having a distilben skeleton disclosed in U.S. Pat. No. 4260672; trisazo pigments having a triphenylamine skeleton disclosed in U.S. Pat. No. 4279981; disazo pigments having a carbazole skeleton disclosed in U.S. Pat. No. 4251614; disazo pigments having a distyrylcarbazole skeleton disclosed in Japan Pat. Appl. Laid-open No. 17734 (1979); disazo pigments having a dibenzothiophene skeleton disclosed in Japan Pat. Appl. Laid-open No. 21728 (1979); disazo pigments having a fluorenone skeleton disclosed in Japan Pat. Appl. Laid-open No. 22834 (1979), disazo pigments having a 2,5-diphenyloxadiazole skeleton disclosed in Japan Pat. Appl. Laid-open Nos. 12742 (1979) and 145142 (1979); disazo pigments having a dibenzothiophene-5,5-dioxide skeleton disclosed in Japan Pat. Appl. Laid-open No. 20736 (1979); disazo pigments having the coupler residue of a naphthalimide skeleton, disclosed in Japan Pat. Appl. Laid-open Nos. 79632 (1979) and 117151 (1980); and monoazo pigments having the coupler residue of a naphthalimide skeleton, disclosed in Japan Pat. Appl. Laid-open No. 17735 (1979). More specifically, the following azo pigments can be cited:

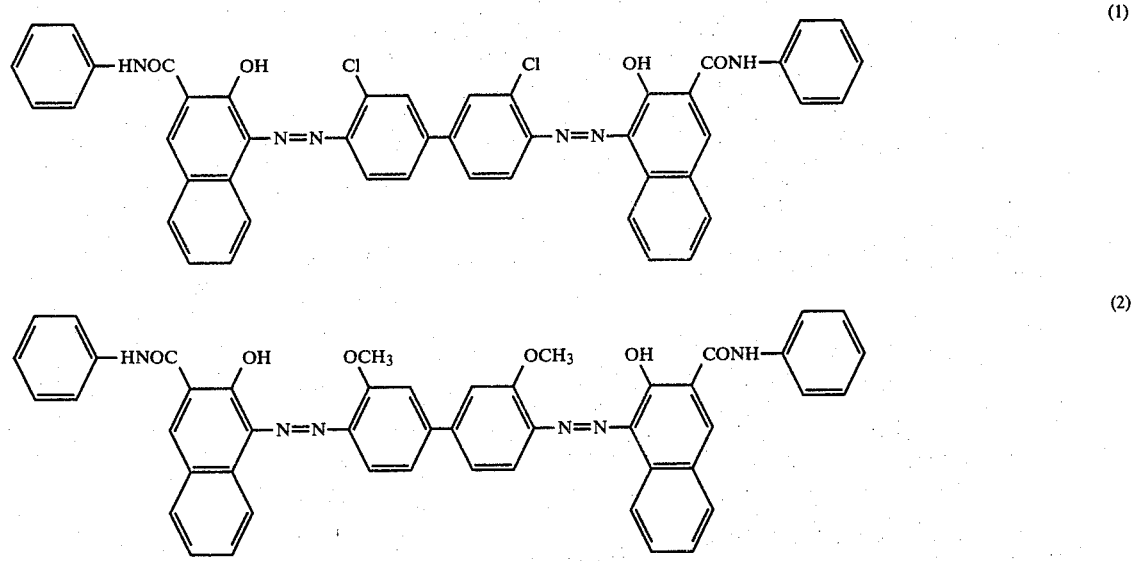

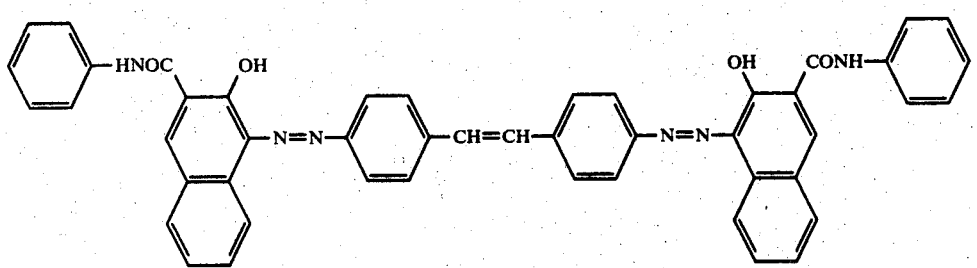
(3)
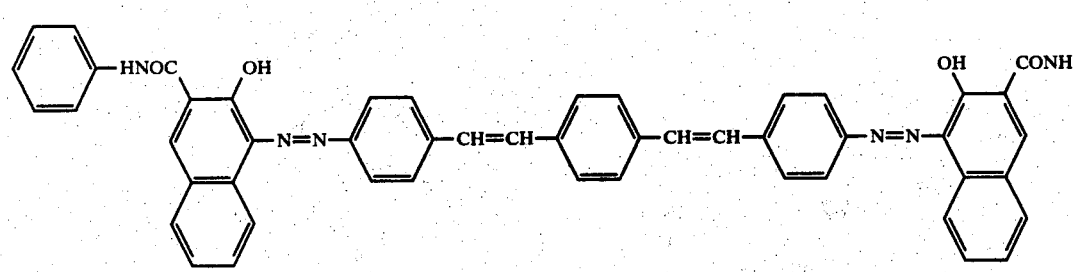
(4)
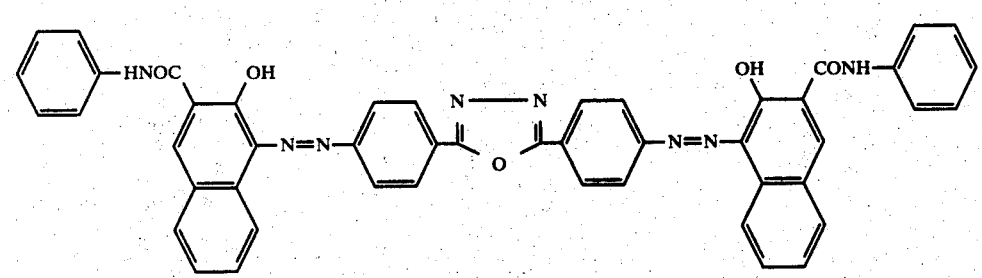
(5)
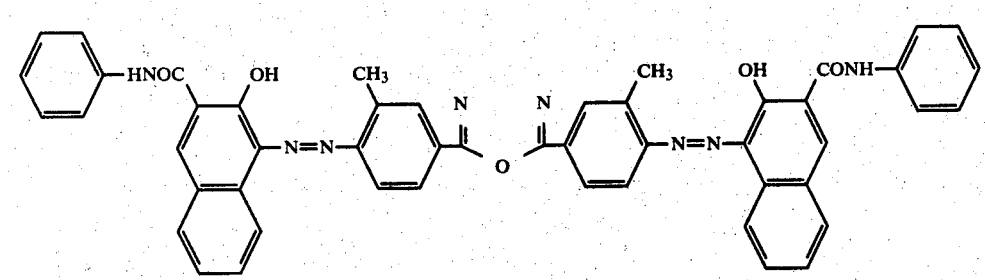
(6)
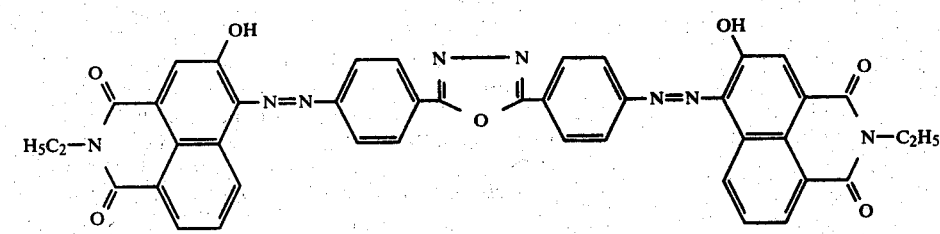
(7)
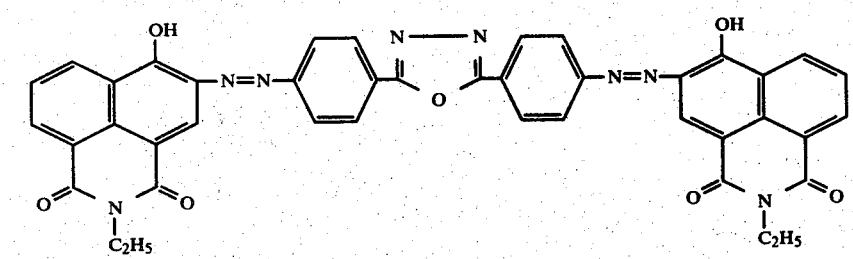
(8)

-continued

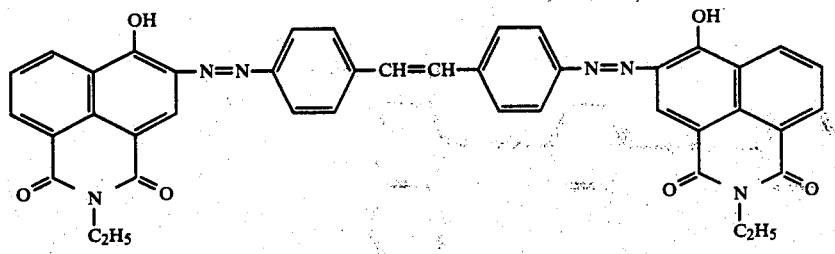 (9)

The following polycyclic quinone pigments can also be cited which have been disclosed in U.S. Pat. No. 3,877,935, and Japan Pat. Appl. Laid-open Nos. 17105 (1980) and 98754 (1980):

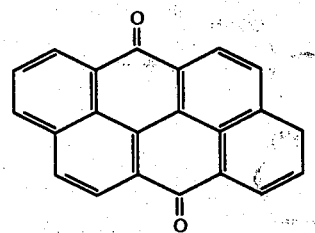 (10)

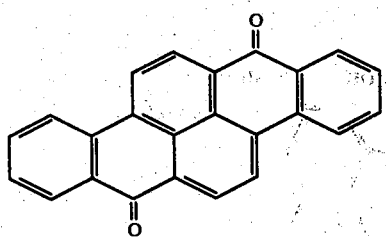 (11)

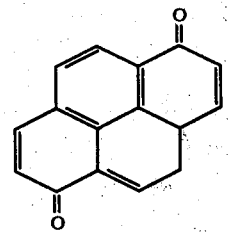 (12)

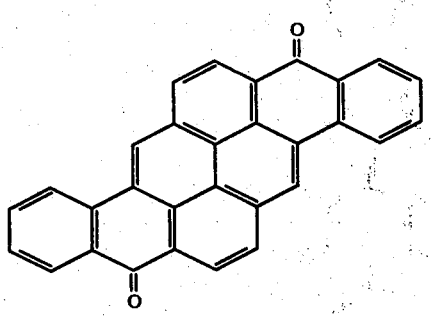 (13)

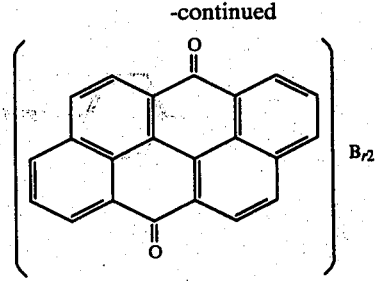 (14)

-continued

The following cyanine dyes can also cited which have been disclosed in Japan Pat. Appl. Laid-open Nos. 41230 (1978), 42830 (1978), 121739 (1979), 121740 (1979), 121741 (1979), and 121742 (1979):

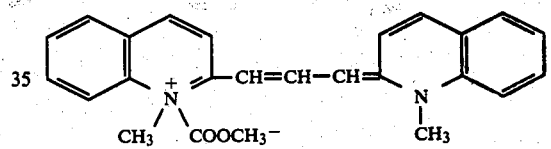 (15)

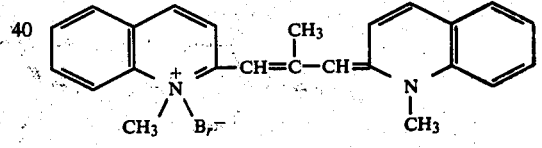 (16)

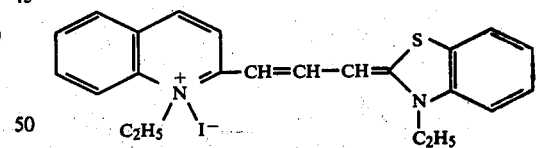 (17)

Further, there may be cited phthalocyanine pigments disclosed in Japan Pat. Appl. Laid-open Nos. 30329 (1972), 11136 (1974), 95852 (1976), 108847 (1976), 109841 (1976), 117637 (1976), and 129234 (1976), e.g., copper phthalocyanines (x-, α-, β-, and ε-types) and derivatives thereof; perylene pigments such as

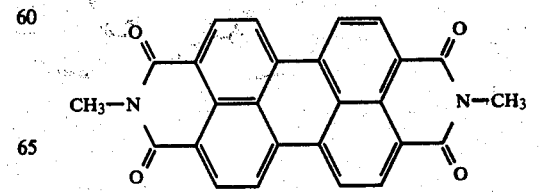 (18)

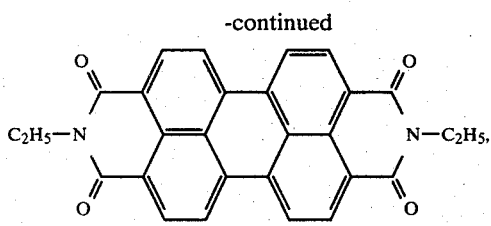
(19)

indigo dyes, and thioindigo dyes, disclosed in Japan Pat. Appl. Laid-open No. 48334 (1974); methyl dyes derived from squaric acid disclosed in U.S. Pat. No. 3,824,099; and an amorphous silicon layer and a vacuum deposited selenium-tellurium layer, disclosed in U.S. Pat. No. 4,265,991 and U.K. Laid-open No. 2018446.

The charge generation layer may be formed in contact with the conductive support mentioned below, or formed on the charge transport layer.

The electrographic photosensitive members of this invention may comprise an intermediate layer on the conductive support, a charge generation layer on said intermediate layer, and a charge transport layer further on the charge generation layer. This intermediate layer acts to prevent the injection of free electric charge from the conductive support to the photosensitive layers when said photoconductive layers having laminate structure are charged and also acts as a bond layer to adhere to both, the support and the photosensitive layer, and keep them in a consolidated state. The materials used for this intermediate layer include aluminum oxide, indium oxide, tin oxide, indium oxide-tin oxide mixtures, polyethylene, polypropylene, acrylic resins, methacrylic resins, vinyl chloride resin, vinyl acetate resin, phenolic resins, epoxy resins, polyester resins, alkyd resins, polycarbonates, polyurethanes, polyimide resin, vinylidene chloride resin, vinyl chloride-vinyl acetate copolymer, casein, and hydroxypropylcellulose. Thickness of this intermediate layer or bond layer is $0.1–5\mu$, preferably $0.5–3\mu$.

When a charge generation layer is formed on a charge transport layer, a metal oxide layer or a polymer layer comprising the above-mentioned material may also be formed as a protective layer for the charge generation layer.

The conductive support to be used in the electrophotographic members of this invention may be of any type conventionally used, as far as it has proper conductivity. For example, metal sheets, vacuum metallized plastic sheets, and metal foil-laminated plastic sheets using the following metals can be cited: aluminum, vanadium, molybdenum, chromium, cadmium, titanium, nickel, copper, zinc, palladium, indium, tin, platinum, gold, stainless steel, and brass.

The hydrazone compounds used in this invention are hole-transporting materials. Consequently, when a photosensitive member prepared by lamination according to the order of a conductive layer, a charge generation layer, and a charge transport layer which employs the hydrazone compounds is operated, the surface of the charge transport layer must be negatively charged. Upon exposing the negatively charged surface to a pattern of light, in the exposed areas holes generated in the charge generation layer are injected into the charge transport layer, then arrive at the surface, and neutralize negative charge to decay the surface potential, thus resulting in an electrostatic contrast between exposed and unexposed areas.

In order to visualize the electrostatic contrast or latent image, various conventional development processes can be applied.

Referring to photosensitive members of other types than (4), description thereof will be omitted because embodiments thereof are described in a number of patent publications and literatures hitherto presented.

The electrophotographic photosensitive members of this invention can be used not only in electrophotographic copying machines but also in a wide variety of application fields such as those of laser printers, CRT printers, and electrophotographic printing plate making systems.

Other types of electrophotographic photosensitive members to which this invention can be applied are cited as follows:

(1) those comprising an organic photoconductor and a co-crystalline complex as main components (U.S. Pat. No. 3,684,502, etc.), (2) those comprising a pigment dispersion in a hole matrix (Japan Pat. Appl. Laid-open No. 18545/1972, etc.), (3) those comprising an organic photoconductor sensitized by addition of a dye (U.S. Pat. No. 3,832,172, etc.), (4) those comprising a charge-transfer complex combining an electron donating substance and an electron attracting substance (Japan Pat. Pub. No. 16197/1968, etc.), (5) those comprising a charge-transfer complex to which an organic or inorganic charge-generating material is added (U.S. Pat. No. 3,775,105, etc.), and the like.

These types of electrophotographic photosensitive members employing the hydrazone compounds of this invention can be prepared in accordance with the processes described in the above-cited patents.

The electrophotographic photosensitive members according to this invention have outstanding improved sensitivity and in addition cause neither an increase of light portion potential nor a decrease of dark portion potential even after charging and exposure are repeated 10,000 times or more.

This invention will be illustrated below by referring to examples.

Example 1

$\beta$-type of copper phthalocyanine pigment (trade name: Linol blue NCB Toner, manufactured by Toyo ink Mfg. Co., Ltd.) was purified by refluxing in water, ethanol, and benzene successively, followed by filtration. A mixture of 7 g of this purified pigment, 14 g of a polyester solution (trade name: Polyester Adhesive 49,000, solid content: 20%, manufactured by Du Pont de Nemours Co.), 35 g of toluene, and 35 g of dioxane was dispersed in a ball mill for 6 hours to obtain a dispersion. The coating dispersion thus prepared was coated on an aluminum sheet by means of a Meyer bar to form a charge generation layer of $0.5\mu$ in dry thickness.

Then, a solution prepared by dissolving 7 g of the above-cited hydrazone compound (2) and 7 g of a polycarbonate resin (trade name: Panlite K-1300, manufactured by Teijin Kasei K.K.) in a mixture solvent of 35 g of tetrahydrofuran and 35 g of chlorobenzene was coated on said charge generation layer to form a charge transport layer of $11\mu$ in dry thickness. The obtained electrophotographic member having a two-layer photosensitive element was designated as sample 1.

Sample 1 was attached to a cylinder in an electrophotographic copying machine and tested for sensitivity and durability. This copying machine is in sequence provided with a negative corona charging device, an optical system for irradiation, a developing device, a charging device for transfer, an exposure optical system for erasing charge, and a cleaner, around the cylinder, and is designed to form an image on transfer paper as the cylinder is driven. The sample attached to the cylinder was charged to have a dark portion potential of $-500$ V and a light portion potential of $-10$ V by adjusting corona charging and exposure.

The sensitivity was evaluated by measuring the light quantity $E_{\frac{1}{2}}$ (lux sec) for halving the potential (V) to which the initially charged potential has been subjected to 5-second dark decay. The durability was evaluated by measuring light portion potential $V_L$ (V) and dark portion potential $V_D$ (V) when image formation was conducted 1, 5,000, 10,000, and 25,000 times. The results are shown in Table 1.

TABLE 1

| | | Durability test | | | | | | | |
|---|---|---|---|---|---|---|---|---|---|
| | | 1-st | | 5,000-th | | 10,000-th | | 25,000-th | |
| Sample | $E_{\frac{1}{2}}$ | $V_D$ | $V_L$ | $V_D$ | $V_L$ | $V_D$ | $V_L$ | $V_D$ | $V_L$ |
| 1 | 5.0 | −500 | −10 | −490 | −15 | −470 | −20 | −470 | −30 |

Examples 2–10

Electrophotographic photosensitive members (samples 2–10) were prepared and tested for sensitivity and durability in the same manner as Example 1, except that the above-cited hydrazone compounds (1) and (3)–(10) were used respectively as charge-transporting materials in place of the hydrazone compound (2). The results are shown in Table 2.

TABLE 2

| | Charge-transporting | | Durability test | | | | | | |
|---|---|---|---|---|---|---|---|---|---|
| | | | 1-st | | 5,000-th | | 10,000-th | | 25,000-th | |
| Sample | compound | $E_{\frac{1}{2}}$ | $V_D$ | $V_L$ | $V_D$ | $V_L$ | $V_D$ | $V_L$ | $V_D$ | $V_L$ |
| 2 | Compound (1) | 16.7 | −450 | −10 | −440 | −10 | −420 | −30 | −390 | −30 |
| 3 | Compound (3) | 7.0 | −510 | −30 | −500 | −30 | −480 | −40 | −480 | −50 |
| 4 | Compound (4) | 6.8 | −480 | −40 | −460 | −40 | −440 | −50 | −420 | −60 |
| 5 | Compound (5) | 6.0 | −550 | −30 | −530 | −30 | −510 | −40 | −480 | −40 |
| 6 | Compound (6) | 13.6 | −580 | −40 | −560 | −40 | −540 | −50 | −530 | −50 |
| 7 | Compound (7) | 6.4 | −650 | −15 | −620 | −10 | −600 | −50 | −610 | −60 |
| 8 | Compound (8) | 15.3 | −500 | −10 | −470 | −10 | −450 | −20 | −440 | −30 |
| 9 | Compound (9) | 5.5 | −500 | −5 | −490 | −5 | −490 | −15 | −480 | −20 |
| 10 | Compound (10) | 5.4 | −400 | −5 | −390 | −5 | −370 | −5 | −370 | −15 |

Comparative Examples 1–5

Electrophotographic photosensitive members (comparative samples 1–5) were prepared and tested for sensitivity and durability in the same manner as Example 1, except that the compounds shown in Table 3 were used respectively as charge-transporting materials in place of the hydrazone compound (2). The results are shown in Table 4.

TABLE 3

| Comparative sample | Charge-transporting compound for comparison |
|---|---|
| 1 | 1, 1-Bis (4-N, N—dibenzylamino-2-methylphenyl) propane |
| 2 | 2, 5-Bis (4-N, N—diethylaminophenyl)-1, 3, 4-oxadiazole |
| 3 | Poly (N—vinylcarbazole) |
| 4 | 1, 1-Bis (4-N, N—diethylamino-2-methylphenyl) heptane |
| 5 | 1-Phenyl-3-(4-N, N—diethylaminostyryl)-5-(4-N, N—diethylaminophenyl) pyrazoline |

TABLE 4

| | | Durability test | | | | | | | |
|---|---|---|---|---|---|---|---|---|---|
| Comparative | | 1-st | | 5,000-th | | 10,000-th | | 25,000-th | |
| sample | $E_{\frac{1}{2}}$ | $V_D$ | $V_L$ | $V_D$ | $V_L$ | $V_D$ | $V_L$ | $V_D$ | $V_L$ |
| 1 | 28.0 | −650 | −150 | −600 | −200 | −510 | −200 | −500 | −250 |
| 2 | 12.5 | −420 | −100 | −420 | −150 | −420 | −200 | −380 | −200 |
| 3 | 15.8 | −720 | −180 | −750 | −200 | −750 | −200 | −450 | −100 |
| 4 | 35.5 | −670 | −200 | −550 | −200 | −500 | −260 | −450 | −280 |
| 5 | 9.5 | −450 | −10 | −400 | −60 | −400 | −70 | −370 | −90 |

As can be seen from Tables 1, 2, and 4, the electrophotographic photosensitive members (samples 1–10) according to this invention have much higher sensitivity as compared with comparative samples 1–5, and show little increase in light portion potential and little decrease in dark portion potential when charging and exposing were repeated,

Example 11

Using the apparatus, shown in FIG. 1, set up in a clean room perfectly shielded, a charge generation layer was formed in the following way:

A molybdenum plate (substrate) 101, having cleaned surface, of 0.2 mm in thickness and 5 cm in dia. was securely fastened to a fixing member 102 located in a definite position in a glow discharge vacuum deposition chamber 109. The substrate 101 was heated to a precision ±0.5° C. by the heater 103 incorporated in the fixing member 102. A thermocouple chromel-alumel thermocouple had been fitted to measure the temperature of the substrate rear surface directly. After confirmation of all valves in the system being closed, a main valve 104 was fully opened to evacuated the chamber 109 to about $5\times10^{-6}$ torr. The input voltage of the heater 103 was raised, and the temperature of the molybdenum substrate was controlled to settle to a constant value of 150° C. with detecting by varying the input voltage.

Then, an auxiliary valve 105 and successively outflow valves 106, 107, and 108 were fully opened to thoroughly evacuate flow meters 110, 111, and 112. The outflow valves 106, 107, and 108 were closed, and the valve 114 of the bomb 103 containing silane gas (99.999% purity) was opened, the pressure of an outlet pressure gage 115 was adjusted to 1 Kg/cm², and an inflow valve 116 was slowly opened to introduce silane gas into the flow meter 110. Successively, the outflow valve 106 was slowly opened, and then the auxiliary valve 105 was slowly opened while watching the reading of a Pirani gauge 117 to raise the pressure in the chamber up to $1\times10^{-2}$ torr. After the pressure in the chamber had settled, the main valve 104 was gradually closed until the indication of the Pirani gauge 117 came to 0.5 torr. After confirmation that the inner pressure had settled, a high frequency power source 118 was turned on to apply high frequency power of 5 MHz to the induction coil 119 and generate glow discharge in the inner space of the chamber 109 surrounded the coil (the upper region of the chamber), where the input power was 30 W. Under these conditions, amorphous silicon was developed on the substrate. After the same conditions had been kept for 1 hour, the high frequency power source 118 was turned off to intermit the glow discharge, the valve of the bomb 120 containing diborane gas (99.999% purity) was turned on, the pressure of a outlet pressure gauge 121 was adjusted to 1 Kg/cm², an inflow valve 122 was slowly opened to introduce diborane gas into the flow meter 111, then the outflow valve 107 was slowly opened and its opening was set so as to keep the flow of diborane gas to 0.08% of the flow of silane gas.

Succeedingly, the high frequency power source 118 was turned on to recommence glow discharge again. The glow discharge was continued for 1 hour, then the heater 103 and the high frequency source 118 were turned off, and after the temperature of the substrate had become 100° C., the outflow valves 106 and 107 were closed, the main valve 104 was fully opened to reduce the pressure in the chamber to $10^{-5}$ torr or less, then the main valve 104 was again closed, and the pressure in the chamber was returned to atmospheric pressure by means of a leak valve 123 to take out the substrate. The total thickness of the amorphous silicon base layer formed on the substrate was about 3μ.

Subsequently, the same charge transport layer as in sample 1 of Example 1 was formed on this amorphous silicon base layer. The electrophotographic photosensitive member thus obtained (sample 11) was tested for sensitivity and durability in the same manner as Example 1. The results are shown in Table 5.

TABLE 5

| Sample | E1/2 | \multicolumn{8}{c}{Durability test} |
|---|---|---|---|---|---|---|---|---|---|
| | | 1-st | | 5,000-th | | 10,000-th | | 25,000-th | |
| | | $V_D$ | $V_L$ | $V_D$ | $V_L$ | $V_D$ | $V_L$ | $V_D$ | $V_L$ |
| 11 | 5.7 | −480 | −15 | −470 | −20 | −440 | −30 | −430 | −40 |

As can be seen from Example 1-11, the electrophotographic photosensitive members according to the present invention have higher sensitivity and improved durability.

Examples 12

An electrophotographic photosensitive member (sample 12) was prepared and tested for sensitivity and durability in the same manner as Example 1, except that the above-cited hydrazone compound (16) was used as a charge-transporting material in place of the compound (2). The results are shown in Table 6.

TABLE 6

| Sample | E1/2 | \multicolumn{8}{c}{Durability test} |
|---|---|---|---|---|---|---|---|---|---|
| | | 1-st | | 5,000-th | | 10,000-th | | 25,000-th | |
| | | $V_D$ | $V_L$ | $V_D$ | $V_L$ | $V_D$ | $V_L$ | $V_D$ | $V_L$ |
| 12 | 4.8 | −500 | −10 | −510 | −20 | −480 | −20 | −470 | −30 |

Examples 13-20

Electrophotographic photosensitive members (samples 13-20) were prepared and tested for sensitivity and durability in the same manner as Example 1, except that the above-cited hydrazone compounds (17)-(24) were used respectively as charge-transporting materials in place of the hydrazone compound (2). The results are shown in Table 7.

TABLE 7

| Sample | Charge-transporting compound | E1/2 | 1-st $V_D$ | $V_L$ | 5,000-th $V_D$ | $V_L$ | 10,000-th $V_D$ | $V_L$ | 25,000-th $V_D$ | $V_L$ |
|---|---|---|---|---|---|---|---|---|---|---|
| 13 | Compound (17) | 4.6 | −480 | −10 | −480 | −10 | −460 | −30 | −450 | −35 |
| 14 | Compound (18) | 4.9 | −490 | −20 | −500 | −20 | −480 | −25 | −470 | −30 |
| 15 | Compound (19) | 7.6 | −530 | −20 | −520 | −30 | −510 | −30 | −500 | −30 |
| 16 | Compound (20) | 15.3 | −560 | −40 | −570 | −40 | −570 | −45 | −550 | −45 |
| 17 | Compound (21) | 5.4 | −500 | −20 | −490 | −30 | −480 | −35 | −480 | −40 |
| 18 | Compound (22) | 8.0 | −540 | −20 | −530 | −30 | −520 | −20 | −510 | −35 |
| 19 | Compound (23) | 5.0 | −520 | −30 | −500 | −35 | −500 | −30 | −490 | −40 |
| 20 | Compound (24) | 5.2 | −530 | −10 | −540 | −20 | −520 | −30 | −520 | −40 |

Example 21

The same charge transport layer as in sample 12 of Example 12 was formed on the amorphous silicon base layer formed in Example 11. The electrophotographic photosensitive member thus prepared (sample 21) was tested for sensitivity and durability in the same fashion as Example 1. The results are shown in Table 8.

TABLE 8

| Sample | E1/2 | 1-st | | 5,000-th | | 10,000-th | | 25,000-th | |
|---|---|---|---|---|---|---|---|---|---|
| | | $V_D$ | $V_L$ | $V_D$ | $V_L$ | $V_D$ | $V_L$ | $V_D$ | $V_L$ |
| 21 | 5.4 | −510 | −20 | −510 | −30 | −490 | −30 | −480 | −40 |

Example 22

A co-crystalline complex was prepared by dissolving 2 g of 4-(4-dimethylaminophenyl)-2, 6-diphenyl-thiapyrylium perchlorate and 2 g of polycarbonate resin (the same as used in Example 1) in 100 ml of dichloromethane, then adding 50 ml of toluene, stirring the solution, further adding 50 ml of dichloromethane to dissolve insoluble matter, thereafter adding 600 ml of n-hexane gradually, followed by filtering and drying the precipitate produced thereby.

Then, 1 g of the co-crystalline complex and 3 g of vinyl butyral resin (trade name: Eslex BM-2, manufactured by Sekisui Chemical Co., Ltd.) were dispersed in 20 ml of toluene and the dispersion was kneaded in a sand mill for 30 minutes. This kneaded matter is added to a solution of 2 g of the above-cited compound (17) of this invention in 30 ml of toluene, and the mixture was further kneaded in a sand mill for 30 minutes.

This kneaded material was coated by use of a Meyer bar on the casein layer of 1μ in thickness formed on an aluminum plate of 100μ in thickness and the coating was dried. Thus, an electrophotographic photosensitive member (sample 22) having a photosensitive layer of 13μ in thickness was obtained.

Charge bearing characteristics of this photosensitive member were measured, using an electrostatic copying paper testing machine (Model SP-428, made by Kawaguchi Denki K.K.), by charging it at an applied voltage of 5 KV in a static fashion and illuminating at 5 lux immediately thereafter. In this case, original charged potential is designated by $V_c$ (V) and exposure quantity for halving original potential is designated by E1/2 (lux.sec). These values are shown in Table 9.

TABLE 9

| Charged polarity | $V_c$ | E1/2 |
|---|---|---|
| ⊖ | ⊖500 | 6.2 |
| ⊕ | ⊕520 | 4.0 |

Example 23

An aqueous solution of hydroxypropylcellulose was coated on an aluminum plate and dried to form a bond layer of 0.6 g/m².

Then, 5 g of a polycarbonate of 4, 4'-dioxydiphenyl-2, 2-propane (viscosity-average mol. wt. about 40,000) and 5 g of the above-cited compound (18) of this invention were dissolved in 150 ml of dichloromethane, and 0.05 g of a pigment having the structure

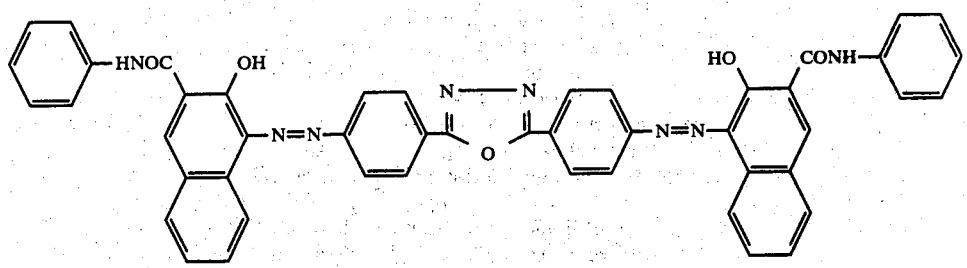

was added to the solution and dispersed in a ball mill. This dispersion was coated on said bond layer, and dried to form a photosensitive layer of 10 g/m².

The electrophotographic photosensitive member (sample 23) thus prepared was tested for charge being characteristics in the same fashion as Example 22, but in this case charging polarity was positive. The results are shown in Table 10.

TABLE 10

| Sample | $V_c$ | E1/2 |
|---|---|---|
| 23 | ⊕ 400 | 16.2 |

Example 24

An electrophotographic photosensitive member (sample 24) was prepared and tested for sensitivity and durability in the same manner as Example 1, except that the above-cited hydrazone compound (25) was used as a charge-transporting material in place of the compound (2). The results are shown in Table 11.

TABLE 11

| Sample | E1/2 | 1-st | | 5,000-th | | 10,000-th | | 25,000-th | |
|---|---|---|---|---|---|---|---|---|---|
| | | $V_D$ | $V_L$ | $V_D$ | $V_L$ | $V_D$ | $V_L$ | $V_D$ | $V_L$ |
| 24 | 3.2 | −500 | −10 | −490 | −5 | −480 | −10 | −480 | −15 |

Examples 25-35

Electrophotographic photosensitive members (samples 25-35) were prepared and tested for sensitivity and durability in the same manner as Example 1, except that the above-cited hydrazone compounds (26)-(36) were used respectively as charge-transporting materials in place of the compound (2). The results are shown in Table 12.

TABLE 12

| Sample | Charge-transporting compound | E1/2 | 1-st $V_D$ | 1-st $V_L$ | 5,000-th $V_D$ | 5,000-th $V_L$ | 10,000-th $V_D$ | 10,000-th $V_L$ | 25,000-th $V_D$ | 25,000-th $V_L$ |
|---|---|---|---|---|---|---|---|---|---|---|
| 25 | Compound (26) | 3.8 | −420 | 0 | −410 | 0 | −430 | −10 | −450 | −30 |
| 26 | Compound (27) | 9.5 | −530 | −20 | −530 | −20 | −500 | −20 | −510 | −35 |
| 27 | Compound (28) | 4.5 | −480 | 0 | −480 | −10 | −450 | −10 | −440 | −15 |
| 28 | Compound (29) | 5.0 | −440 | 0 | −420 | −20 | −420 | −25 | −430 | −25 |
| 29 | Compound (30) | 2.9 | −410 | 0 | −410 | −5 | −420 | −20 | −400 | −25 |
| 30 | Compound (31) | 8.5 | −500 | −20 | −540 | −30 | −510 | −30 | −490 | −30 |
| 31 | Compound (32) | 10.0 | −580 | −30 | −570 | −30 | −560 | −20 | −550 | −30 |
| 32 | Compound (33) | 6.5 | −490 | −10 | −490 | −20 | −440 | −30 | −450 | −35 |
| 33 | Compound (34) | 3.7 | −440 | 0 | −440 | −10 | −410 | −15 | −410 | −20 |
| 34 | Compound (35) | 4.0 | −420 | 0 | −400 | 0 | −400 | −10 | −390 | −15 |
| 35 | Compound (36) | 6.0 | −520 | −20 | −550 | −25 | −540 | −30 | −490 | −20 |

Example 36

The same charge transport layer as in sample 24 of Example 24 was formed on the amorphous silicon base layer formed in Example 11. The electrophotographic member thus prepared (sample 36) was tested for sensitivity and durability in the same manner as Example 1. The results are shown in Table 13.

TABLE 13

| Sample | E1/2 | 1-st $V_D$ | 1-st $V_L$ | 5,000-th $V_D$ | 5,000-th $V_L$ | 10,000-th $V_D$ | 10,000-th $V_L$ | 25,000-th $V_D$ | 25,000-th $V_L$ |
|---|---|---|---|---|---|---|---|---|---|
| 36 | 7.8 | −320 | 0 | −320 | 0 | −330 | −20 | −350 | −40 |

Example 37

A dispersion was prepared by dispersing 5 g of purified chloro-dianeblue [3, 3'-dichloro-4, 4'-diphenyl-bis(1"-azo-2"-hydroxy-3"-naphanilide)](C.I. 21180) in a solution of 2 g of vinyl butyral resin (the same as used in Example 22) in 50 g of ethanol, followed by mixing and grinding in a ball mill for 30 hours. This dispersion was coated on an aluminum plate to form a charge generation layer of 0.2μ in dry thickness.

Then, the same charge transport layer as in sample 24 of Example 24 was formed on this charge generation layer.

The electrophotographic photosensitive member thus prepared (sample 37) was tested for sensitivity and durability in the same fashion as Example 1. The results are shown in Table 14.

TABLE 14

| Sample | E1/2 | 1-st $V_D$ | 1-st $V_L$ | 5,000-th $V_D$ | 5,000-th $V_L$ | 10,000-th $V_D$ | 10,000-th $V_L$ | 25,000-th $V_D$ | 25,000-th $V_L$ |
|---|---|---|---|---|---|---|---|---|---|
| 37 | 4.5 | −440 | 0 | −420 | −10 | −420 | −20 | −400 | −10 |

Example 38

An electrophotographic photosensitive member (sample 38) was prepared and tested for sensitivity and durability in the same manner as Example 1, except that the above-cited compound (37) was used as a charge-transporting material in place of the compound (2). The results are shown in Table 15.

TABLE 15

| Sample | E1/2 | 1-st $V_D$ | 1-st $V_L$ | 5,000-th $V_D$ | 5,000-th $V_L$ | 10,000-th $V_D$ | 10,000-th $V_L$ | 25,000-th $V_D$ | 25,000-th $V_L$ |
|---|---|---|---|---|---|---|---|---|---|
| 38 | 5.2 | −500 | −10 | −490 | −10 | −480 | −15 | −480 | −20 |

Examples 39-46

Electrophotographic photosensitive members (samples 39-46) were prepared and tested for sensitivity and durability in the same manner as Example 1, except that the above-cited hydrazone compounds (38)-(45) were used respectively as charge-transporting materials in place of the compound (2). The results are shown in Table 16.

TABLE 16

| Sample | Charge-transporting compound | E½ | Durability test | | | | | | | |
|---|---|---|---|---|---|---|---|---|---|---|
| | | | 1-st | | 5,000-th | | 10,000-th | | 25,000-th | |
| | | | $V_D$ | $V_L$ | $V_D$ | $V_L$ | $V_D$ | $V_L$ | $V_D$ | $V_L$ |
| 39 | Compound (38) | 5.0 | −520 | −10 | −520 | −10 | −510 | −20 | −500 | −20 |
| 40 | Compound (39) | 4.8 | −490 | 0 | −500 | −10 | −480 | −20 | −470 | −30 |
| 41 | Compound (40) | 3.2 | −450 | 0 | −460 | −10 | −440 | −10 | −430 | −20 |
| 42 | Compound (41) | 4.6 | −500 | −20 | −520 | −20 | −500 | −25 | −480 | −30 |
| 43 | Compound (42) | 5.6 | −560 | −20 | −550 | −30 | −540 | −30 | −530 | −30 |
| 44 | Compound (43) | 5.4 | −550 | −10 | −530 | −10 | −530 | −10 | −520 | −20 |
| 45 | Compound (44) | 6.5 | −580 | −30 | −570 | −30 | −560 | −30 | −560 | −35 |
| 46 | Compound (45) | 3.9 | −470 | 0 | −460 | −10 | −460 | −10 | −450 | −20 |

Example 47

The same charge transport layer as in sample 38 of Example 38 was formed on the amorphous silicon base layer prepared in Example 11. The electrophotographic member thus prepared (sample 47) was tested for sensitivity and durability in the same fashion as Example 1. The results are shown in Table 17.

on an aluminum plate by use of a Meyer bar and dried to form a bond layer of 1.0 g/m².

A dispersion was prepared by mixing and grinding in a ball mill 5 g of a pigment having the formula

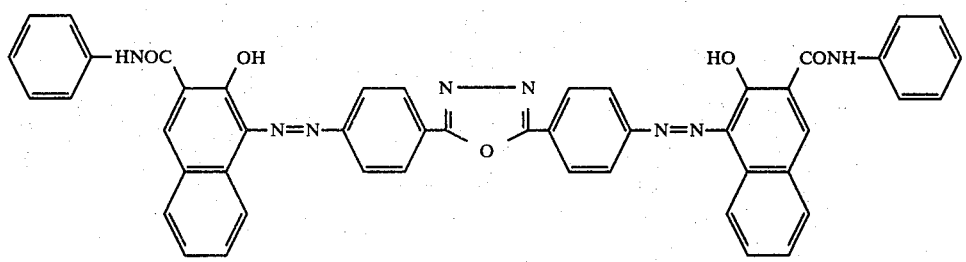

with a solution of 2 g of a vinyl butyral resin (degree of butyral conversion 63 mol %) in 95 ml of ethanol, and was coated on said bond layer by use of a Meyer bar to form a charge generation layer of 0.2 g/m² after drying.

TABLE 17

| Sample | E½ | Durability test | | | | | | | |
|---|---|---|---|---|---|---|---|---|---|
| | | 1-st | | 5,000-th | | 10,000-th | | 25,000-th | |
| | | $V_D$ | $V_L$ | $V_D$ | $V_L$ | $V_D$ | $V_L$ | $V_D$ | $V_L$ |
| 47 | 7.6 | −330 | 0 | −330 | 0 | −350 | −20 | −350 | −30 |

Example 48

The same charge transport layer as in sample 38 of Example 38 was formed on the charge generation layer prepared in Example 37, and the electrophotographic photosensitive member thus prepared (sample 48) was tested for sensitivity and durability in the same manner as Example 1. The results are shown in Table 18.

Then, a solution prepared by dissolving 5 g of the above-cited hydrazone compound (2) and 5 g of a polycarbonate resin (mol. wt. about 30,000) of 4, 4'-dioxydiphenyl-2, 2-propane in 300 ml of dichloromethane was coated on said charge generation layer to form a charge transport layer of 10 g/m² after drying.

The electrophotographic photosensitive member thus prepared (sample 49) was tested for sensitivity and

TABLE 18

| Sample | E½ | Durability test | | | | | | | |
|---|---|---|---|---|---|---|---|---|---|
| | | 1-st | | 5,000-th | | 10,000-th | | 25,000-th | |
| | | $V_D$ | $V_L$ | $V_D$ | $V_L$ | $V_D$ | $V_L$ | $V_D$ | $V_L$ |
| 48 | 4.3 | −480 | −10 | −470 | −10 | −450 | −20 | −450 | −25 |

Example 49

A solution of casein in aqueous ammonia (casein 11.2 g, 28% aqueous ammonia 1 g, water 222 ml) was coated durability in the same manner as Example 1. The results are shown in Table 19.

TABLE 19

| Sample | E½ | Durability test | | | | | | | |
|---|---|---|---|---|---|---|---|---|---|
| | | 1-st | | 5,000-th | | 10,000-th | | 25,000-th | |
| | | $V_D$ | $V_L$ | $V_D$ | $V_L$ | $V_D$ | $V_L$ | $V_D$ | $V_L$ |
| 49 | 4.6 | −510 | −10 | −500 | −10 | −470 | −20 | −470 | −30 |

Example 50

An electrophotographic photosensitive member (sample 50) was prepared in the same manner as Example 49, except that the above-cited hydrazone compound (16) was used in place of the hydrazone compound (2). This sample was tested for sensitivity and durability in the same manner as Example 1, and similar results was obtained.

Example 51

A solution of casein in aqueous ammonia (the same as in Example 49) was coated on an aluminum plate and dried to form a bond layer of 1.0 g/m².

Then, a dispersion of 5 g of a pigment having the formula

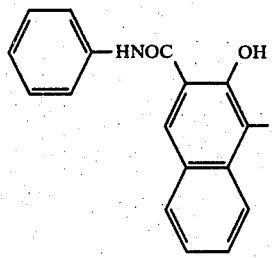

10 g of a polyester resin solution (the same as used in Example 1) and 80 ml of tetrahydrofuran was coated on said bond layer to form a charge generation layer of 0.25 g/m² after drying.

Further, a solution prepared by dissolving 5 g of the above-cited hydrazone compound (9) and 5 g of a poly(methyl methacrylate)resin (mol. wt. about 100,000) in 100 ml of dichloroethane was coated on said charge generation layer to form a charge transport layer of 10 g/m² after drying.

The electrophotographic photosensitive member thus prepared (sample 51) was tested for sensitivity and durability in the same mamner as Example 1. The results are shown in Table 20.

TABLE 20

| | | Durability test | | | | | | |
|---|---|---|---|---|---|---|---|---|
| | | 1-st | | 5,000-th | | 10,000-th | | 25,000-th |
| Sample | E½ | $V_D$ | $V_L$ | $V_D$ | $V_L$ | $V_D$ | $V_L$ | $V_D$ $V_L$ |
| 51 | 5.7 | −500 | −10 | −500 | −15 | −470 | −20 | −470 −20 |

Examples 52–54

Electrophotographic photosensitive members (samples 52, 53, and 54) were prepared in the same manner as Example 51, except that the above-cited hydrazone compounds (18), (28), and (40) were used respectively in place of the hydrazone compound (9).

These samples were tested for sensitivity and durability in the same manner as Example 1, and all gave similar results.

Example 55

A pigment having the structure

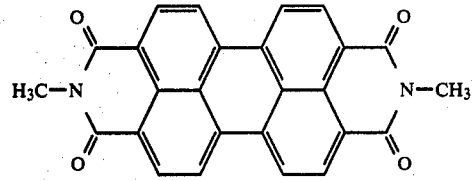

was vacuum-deposited on an aluminum plate of 100μ in thickness to form a charge generation layer of 0.15μ thickness.

Then, a solution prepared by dissolving 5 g of a polyester resin (Vylon 200, manufactured Toyobo Co., Ltd.) and 5 g of the above-cited hydrazone compound (2) in 150 ml of dichloromethane was coated on said charge generation layer and dried to form a charge transport layer of 11 g/m².

The electrophotographic photosensitive member thus prepared (sample 55) was tested for sensitivity and durability in the same manner as Example 1. The results are shown in Table 21.

TABLE 21

| | | Durability test | | | | | | |
|---|---|---|---|---|---|---|---|---|
| | | 1-st | | 5,000-th | | 10,000-th | | 25,000-th |
| Sample | E½ | $V_D$ | $V_L$ | $V_D$ | $V_L$ | $V_D$ | $V_L$ | $V_D$ $V_L$ |
| 55 | 8.8 | −510 | −10 | −500 | −10 | −470 | −15 | −460 −20 |

Examples 56 and 57

Electrophotographic photosensitive members (samples 56 and 57) were prepared in the same manner as Example 55, except that the above-cited hydrazone compounds (18) and (28) were used respectively in place of the hydrazone compound (2). These samples were tested for sensitivity and durability in the same manner as Example 1, and both gave similar results.

What we claim is:

1. An electrophotographic photosensitive member characterized by having a conductive support and a layer containing at least one hydrazone compound represented by the following formula [I] or [II]:

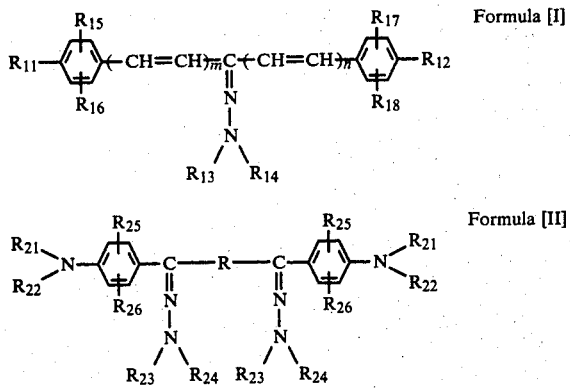

Formula [I]

Formula [II]

wherein $R_{11}$ and $R_{12}$ represent hydrogen, halogen, substituted or unsubstituted alkyl, alkoxy, substituted or unsubstituted aryloxy, or substituted amino, provided that at least one of $R_{11}$ and $R_{12}$ is substituted amino or alkoxy; $R_{13}$ and $R_{14}$ represent substituted or unsubstituted alkyl or substituted or unsubstituted aryl, provided that at least one of $R_{13}$ and $R_{14}$ is substituted or unsubstituted aryl, or $R_{13}$ and $R_{14}$, together with the nitrogen atom which links them, represent a nitrogen-containing heterocyclic ring; $R_{15}$, $R_{16}$, $R_{17}$, and $R_{18}$ represent hydrogen, halogen, substituted or unsubstituted alkyl, alkoxy, substituted or unsubstituted aryloxy, or substituted amino; m and n represent 0 or 1; $R_{21}$ and $R_{22}$, represent substituted or unsubstituted alkyl, or substituted or unsubstituted aryl, or $R_{21}$ and $R_{22}$, together with the nitrogen atom which links them, represent a five- or six-membered ring; $R_{23}$ and $R_{24}$ represent substituted or unsubstituted alkyl, substituted or unsubstituted aryl, or $R_{23}$ and $R_{24}$, together with the nitrogen atom which links them, represent a five- or six-membered ring; $R_{25}$ and $R_{26}$ represent hydrogen, halogen, nitro, substituted or unsubstituted alkyl, alkoxy, substituted or unsubstituted aryloxy, substituted or unsubstituted acyl, or substituted or unsubstituted amino; and R represents divalent organic residue.

2. An electrophotographic photosensitive member according to claim 1, wherein said hydrazone compound is represented by the following formula (1):

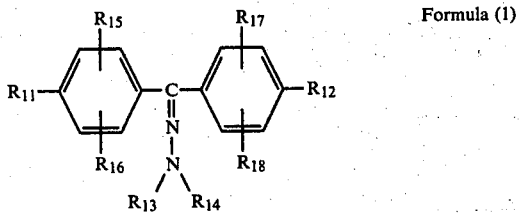

Formula (1)

wherein, $R_{11}$ and $R_{12}$ represent hydrogen, halogen, substituted or unsubstituted alkyl, alkoxy, substituted or unsubstituted aryloxy, or substituted amino, provided that at least one of $R_{11}$ and $R_{12}$ is substituted amino, or alkoxy; $R_{13}$ and $R_{14}$ represent substituted or unsubstituted alkyl or substituted or unsubstituted aryl, provided that at least one of $R_{13}$ and $R_{14}$ is substituted or unsubstituted aryl, or $R_{13}$ and $R_{14}$, together with the nitrogen atom which links them, represent a nitrogen-containing heterocyclic ring; and $R_{15}$, $R_{16}$, $R_{17}$, and $R_{18}$ represent hydrogen, halogen, substituted or unsubstituted alkyl, alkoxy, substituted or unsubstituted aryloxy, or substituted amino.

3. An electrophotographic photosensitive member according to claim 2, wherein $R_{11}$ and $R_{12}$ are radicals selected from alkoxy and substituted amino.

4. An electrophotographic photosensitive member according to claim 3, wherein $R_{11}$ and $R_{12}$ are each substituted amino.

5. An electrophotographic photosensitive member according to claim 4, wherein $R_{11}$ and $R_{12}$ are radicals selected from N,N-dimethylamino, N,N-diethylamino, N,N-dipropylamino, N,N-dibutylamino, and N,N-dibenzylamino.

6. An electrophotographic photosensitive member according to claim 5, wherein $R_{11}$ and $R_{12}$ are each diethylamino.

7. An electrophotographic photosensitive member according to claim 3, wherein $R_{11}$ and $R_{12}$ are each alkoxy.

8. An electrophotographic photosensitive member according to claim 7, wherein $R_{11}$ and $R_{12}$ are radicals selected from methoxy and ethoxy.

9. An electrophotographic photosensitive member according to claim 2, wherein $R_{15}$, $R_{16}$, $R_{17}$, and $R_{18}$ are each hydrogen.

10. An electrophotographic photosensitive member according to claim 9, wherein at least one of $R_{13}$ and $R_{14}$ is phenyl.

11. An electrophotographic photosensitive member according to claim 10, wherein $R_{13}$ is a radical selected from methyl and ethyl.

12. An electrophotographic photosensitive member according to claim 10, wherein $R_{13}$ and $R_{14}$ are each phenyl.

13. An electrophotographic photosensitive member according to claim 2, wherein $R_{13}$ and $R_{14}$, together with the nitrogen atom which links them, represent carbazole ring.

14. An electrophotographic photosensitive member according to claim 1, wherein said hydrazone compound is represented by the following formula (2):

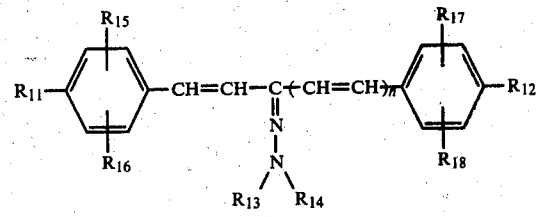

wherein $R_{11}$ and $R_{12}$ represent hydrogen, halogen, substituted or unsubstituted alkyl, alkoxy, substituted or unsubstituted aryloxy, or substituted amino, provided that at least one of $R_{11}$ and $R_{12}$ is substituted amino or alkoxy; $R_{13}$ and $R_{14}$ represent substituted or unsubstituted alkyl or substituted or unsubstituted aryl, provided that at least one of $R_{13}$ and $R_{14}$ is substituted or unsubstituted aryl, or $R_{13}$ and $R_{14}$, together with the nitrogen atom which links them, represent a nitrogen-containing heterocyclic ring; $R_{15}$, $R_{16}$, $R_{17}$, and $R_{18}$ represent hydrogen, halogen, substituted or unsubstituted alkyl, alkoxy, substituted or unsubstituted aryloxy, or substituted amino; and n represent 0 or 1.

15. An electrophotographic photosensitive member according to claim 14, wherein $R_{11}$ and $R_{12}$ are radicals selected from alkoxy and substituted amino.

16. An electrophotographic photosensitive member according to claim 15, wherein $R_{11}$ and $R_{12}$ are each substituted amino.

17. An electrophotographic photosensitive member according to claim 16, wherein $R_{11}$ and $R_{12}$ are radicals selected from N,N-dimethylamino, N,N-diethylamino, N,N-dipropylamino, N,N-dibutylamino, and N,N-dibenzylamino.

18. An electrophotographic photosensitive member according to claim 17, wherein $R_{11}$ and $R_{12}$ are each diethylamino.

19. An electrophotographic photosensitive member according to claim 15, wherein $R_{11}$ and $R_{12}$ are each ethoxy.

20. An electrophotographic photosensitive member according to claim 14, wherein $R_{15}$, $R_{16}$, $R_{17}$, and $R_{18}$ are each hydrogen.

21. An electrophotographic photosensitive member according to claim 20, wherein n is 0.

22. An electrophotographic photosensitive member according to claim 20, wherein n is 1.

23. An electrophotographic photosensitive member according to claim 20, wherein at least one of $R_{13}$ and $R_{14}$ is phenyl.

24. An electrophotographic photosensitive member according to claim 23, wherein $R_{13}$ and $R_{14}$ are each phenyl.

25. An electrophotographic photosensitive member according to claim 23, wherein $R_{13}$ is methyl or naphthyl.

26. An electrophotographic photosensitive member according to claim 14, wherein $R_{13}$ and $R_{14}$, together with the nitrogen atom which links them, represent carbazole ring.

27. An electrophotographic photosensitive member according to claim 1, wherein said hydrazone compound is represented by formula [II] of which R is a substituted or unsubstituted divalent hydrocarbon radical.

28. An electrophotographic photosensitive member according to claim 27, wherein R is a divalent hydrocarbon radical selected from the group consisting of —(CH$_2$)$_{n1}$— ($n_1$ is an integer of 1-15), (A)
—(CH=CH)$_{n2}$— ($n_2$ is an integer of 1-3), (B)

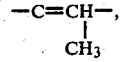 (C)

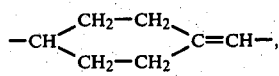 (D)

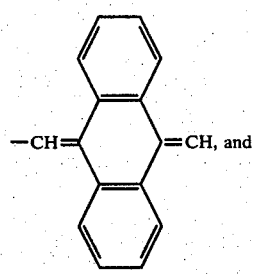 (E)

-continued

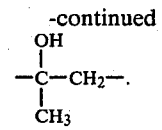 (F)

29. An electrophotographic photosensitive member according to claim 27, wherein R is substituted or unsubstituted arylene.

30. An electrophotographic photosensitive member according to claim 29, wherein R is a divalent hydrocarbon radical selected from

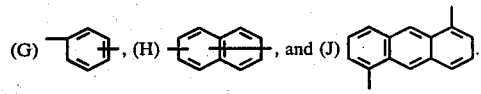

31. An electrophotographic photosensitive member according to claim 27, wherein $R_{21}$ and $R_{22}$ are radicals selected from the group consisting of methyl, ethyl, propyl, butyl, and benzyl.

32. An electrophotographic photosensitive member according to claim 31, wherein $R_{21}$ and $R_{22}$ are each ethyl.

33. An electrophotographic photosensitive member according to claim 27, wherein $R_{21}$ and $R_{22}$, together with the nitrogen atom which links them, represent a ring selected from the group consisting of piperidine ring, morpholine, and pyrrolidine ring.

34. An electrophotographic photosensitive member according to claim 27, wherein at least one of $R_{23}$ and $R_{24}$ is phenyl.

35. An electrophotographic photosensitive member according to claim 34, wherein $R_{23}$ and $R_{24}$ are each phenyl.

36. An electrophotographic photosensitive member according to claim 34, wherein $R_{23}$ is methyl.

37. An electrophotographic photosensitive member according to claim 27, wherein $R_{25}$ and $R_{26}$ are each hydrogen.

38. An electrophotographic photosensitive member according to claim 1, wherein a layer containing at least one hydrazone compound represented by formula [I] or [II] has a function to transport charge generated in a charge generation layer.

39. An electrophotographic photosensitive member according to claim 38, wherein said charge comprises holes.

40. An electrophotographic photosensitive member according to claim 38, wherein the layer containing at least one hydrazone compound represented by formula [I] or [II] is provided in contiguity with said charge generation layer.

41. An electrophotographic photosensitive member according to claim 40, wherein the layer containing at least one hydrazone compound represented by formula [I] or [II] is laid on said charge generation layer.

42. An electrophotographic photosensitive member according to claim 38, wherein said charge generation layer contains a compound selected from the group consisting of disazo pigments, trisazo pigments, pyrylium dyes, thiopyrylium dyes, triarylmethane dyes, thiazine dyes, cyanine dyes, phthalocyanine dyes, perylene pigments, indigo dyes, thioindigo dyes, quinacridone pigments, squaric acid pigments, and polycyclic quinone pigments.

43. An electrophotographic photosensitive member according to claim 42, wherein said charge generation layer comprises a disazo pigment and a binder.

44. An electrophotographic photosensitive member according to claim 42, wherein said phthalocyanine dye is copper phthalocyanine.

45. An electrophotographic photosensitive member according to claim 38, wherein said charge generation layer comprises an amorphous silicon base film.

46. An electrophotographic photosensitive member according to claim 45, wherein said amorphous silicon base film is a deposit formed by glow discharge.

47. An electrophotographic photosensitive member according to claim 38, wherein said charge generation layer comprises a vacuum deposition film of perylene pigment.

48. An electrophotographic photosensitive member according to claim 1, wherein the layer containing at least one hydrazone compound represented by formula [I] or [II] contains a co-crystalline complex of thiapyrylium dye and polycarbonate resin.

49. An electrophotographic photosensitive member according to claim 1, wherein the layer containing at least one hydrazone compound represented by formula [I] or [II] contains a charge-generating material.

50. An electrophotographic photosensitive member characterized by having a conductive support, a charge generation layer and a charge transport layer to transport the charge generated in said charge generation layer, said charge transport layer containing at least one hydrazone compound represented by the following formula [I] or [II]:

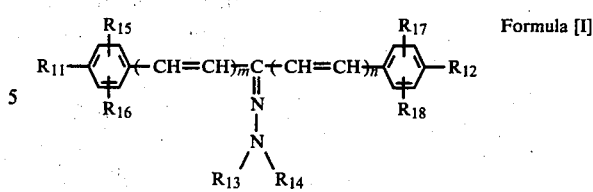

Formula [I]

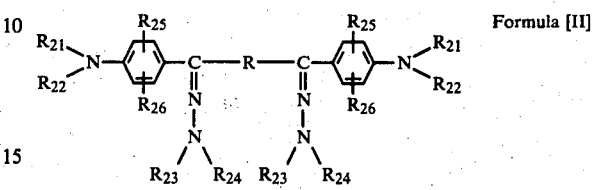

Formula [II]

wherein $R_{11}$ and $R_{12}$ represent hydrogen, halogen, substituted or unsubstituted alkyl, alkoxy, substituted or unsubstituted aryloxy, or substituted amino, provided that at least one of $R_{11}$ and $R_{12}$ is substituted amino or alkoxy; $R_{13}$ and $R_{14}$ represent substituted or unsubstituted alkyl or substituted or unsubstituted aryl, provided that at least one of $R_{13}$ and $R_{14}$ is substituted or unsubstituted aryl, or $R_{13}$ and $R_{14}$, together with the nitrogen atom which links them, represent a nitrogen-containing heterocyclic ring; $R_{15}$, $R_{16}$, $R_{17}$, and $R_{18}$ represent hydrogen, halogen, substituted or unsubstituted alkyl, alkoxy, substituted or unsubstituted aryloxy, or substituted amino; m and n represent 0 or 1; $R_{21}$ and $R_{22}$, represent substituted or unsubstituted alkyl, or substituted or unsubstituted aryl, or $R_{21}$ and $R_{22}$, together with the nitrogen atom which links them, represent a five- or six-membered ring; $R_{23}$ and $R_{24}$ represent substituted or unsubstituted alkyl, substituted or unsubstituted aryl, or $R_{23}$ and $R_{24}$, together with the nitrogen atom which links them, represent a five- or six-membered ring; $R_{25}$ and $R_{26}$ represent hydrogen, halogen, nitro, substituted or unsubstituted alkyl, alkoxy, substituted or unsubstituted aryloxy, substituted or unsubstituted acyl, or substituted or unsubstituted amino; and R represents divalent organic residue.

51. The electrophotographic photosensitive member according to claim 50 wherein an intermediate layer is spaced between said conductive support and said charge generation layer.

* * * * *

UNITED STATES PATENT AND TRADEMARK OFFICE
CERTIFICATE OF CORRECTION

PATENT NO. : 4,399,208    Page 1 of 2
DATED : August 16, 1983
INVENTOR(S) : TAKASU, ET AL.

It is certified that error appears in the above-identified patent and that said Letters Patent is hereby corrected as shown below:

Col. 1, line 17, after "contrast" insert --to--.
Col. 1, line 22, "are lack of" should be --lack--.
Col. 1, line 55, "have offered" should be --have been offered--.
Col. 2, line 31, "members" should be --member--.
Col. 4, line 24, "chlorophenyl" should be --chlorophenoxy--.
Col. 4, line 34, after "hydroxyl" delete --hydroxy--.
Col. 21, line 32, "stirred" should be --stirring--.
Col. 21, line 67, "one-hour" should be --one-hour of--.
Col. 22, line 30, "favarable" should be --favorable--.
Col. 28, line 27, after "also" insert --be--.

Col. 30, line 51, "ink" should be --Ink--.
Col. 30, line 65, "mixture" should be --mixed--.
Col. 33, line 2, "evacuated" should be --evacuate--.
Col. 33, line 14, "gage" should be --gauge--.
Col. 33, line 34, "surrounded" should be --surrounding--.
Col. 33, line 50, "a" should be --an--.
Col. 34, line 27, "Example" should be --Examples--.
Col. 35, line 44, "is" should be --was--.
Col. 36, line 43, "being" should be --bearing--.
Col. 41, line 9, "was" should be --were--.

UNITED STATES PATENT AND TRADEMARK OFFICE
CERTIFICATE OF CORRECTION

PATENT NO. : 4,399,208

DATED : August 16, 1983

INVENTOR(S) : TAKASU, ET AL.

It is certified that error appears in the above-identified patent and that said Letters Patent is hereby corrected as shown below:

Col. 42, line 30, "manufactured Toyobo" to --manufactured by Toyobo--.

Col. 45, line 63,

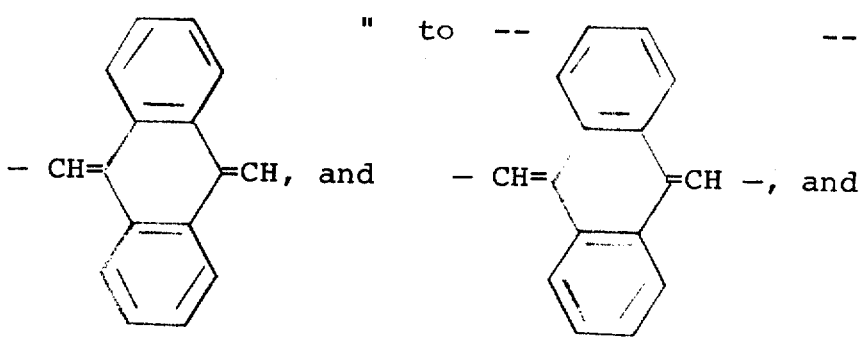

Signed and Sealed this

Twentieth Day of March 1984

[SEAL]

Attest:

Attesting Officer

GERALD J. MOSSINGHOFF

Commissioner of Patents and Trademarks